United States Patent
Ambrus et al.

(10) Patent No.: US 9,540,328 B2
(45) Date of Patent: *Jan. 10, 2017

(54) (−)-(2R,3S)-2-AMINO-3-HYDROXY-3-PYRIDIN-4-YL-1-PYRROLIDIN-1-YL-PROPAN-1-ONE (L)-(+) TARTRATE SALT, ITS METHOD OF PRODUCTION AND USE

(71) Applicant: Allergan, Inc., Irvine, CA (US)

(72) Inventors: Gyorgy F. Ambrus, Santa Ana, CA (US); Katherine C. Kurjan, Huntington Beach, CA (US); Jacopo Zanon, Venice (IT); Giovanna Libralon, Lugano (CH); Carla De Faveri, Farra di Soligo (IT)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/976,926

(22) Filed: Dec. 21, 2015

(65) Prior Publication Data
US 2016/0347712 A1    Dec. 1, 2016

Related U.S. Application Data

(63) Continuation of application No. 14/459,551, filed on Aug. 14, 2014, now Pat. No. 9,242,935.

(60) Provisional application No. 61/866,155, filed on Aug. 15, 2013.

(51) Int. Cl.
C07D 213/56    (2006.01)
C07D 401/02    (2006.01)
A61K 31/44     (2006.01)
C07C 59/255    (2006.01)

(52) U.S. Cl.
CPC .......... *C07D 213/56* (2013.01); *C07C 59/255* (2013.01)

(58) Field of Classification Search
None
See application file for complete search history.

(56) References Cited

U.S. PATENT DOCUMENTS 9,242,935 B2    1/2016    Ambrus et al.

FOREIGN PATENT DOCUMENTS

| WO | 2006-081273 | 8/2006 |
| WO | 2008-011478 | 1/2008 |
| WO | 2008-109610 | 9/2008 |

OTHER PUBLICATIONS

Dixon, W.J., Efficient Analysis of Experimental Observations, Ann. Rev. Pharacol. Toxicol. 1980, 20: 441-462.
Kim, S.H. et al., An experimental model for peripheral neuropathy produced by segmental spinal nerve ligation in the rat, Pain 1992, 50: 355-403.
International Search Report & Written Opinion mailed on Sep. 30, 2014 for PCT/US2014/051007 filed on Aug. 14, 2014 in the name of Allergan, Inc.

*Primary Examiner* — Zinna Northington Davis
(74) *Attorney, Agent, or Firm* — Jonathan Bass

(57) ABSTRACT

The present invention is directed to (−)-(2R,3S)-2-amino-3-hydroxy-3-pyridin-4-yl-1-pyrrolidin-1-yl-propan-1-one (L)-(+) tartrate salt, a pharmaceutical composition comprising said salt, a process for making said salt, and the use of said salt in the treatment of pain.

11 Claims, 18 Drawing Sheets

(−)-(2R,3S)-2-AMINO-3-HYDROXY-3-PYRIDIN-4-YL-1-PYRROLIDIN-1-YL-PROPAN-1-ONE (L)-(+) TARTRATE SALT, ITS METHOD OF PRODUCTION AND USE

CROSS REFERENCE TO RELATED APPLICATIONS

This application is a continuation of U.S. patent application Ser. No. 14/459,551, filed Aug. 14, 2014, which in turn claims the benefit of U.S. Provisional Application Ser. No. 61/866,155 filed on Aug. 15, 2013, each of which are hereby incorporated herein by reference in their entireties, and serve as the basis for a priority and/or benefit claim of the present application.

FIELD OF THE INVENTION

The present invention relates to (−)-(2R,3S)-2-amino-3-hydroxy-3-pyridin-4-yl-1-pyrrolidin-1-yl-propan-1-one (L)-(+) tartrate salt (i.e., the monotartrate salt), its synthesis and use as an analgesic in the treatment of pain, or its use in the treatment of a cognitive disorder.

DESCRIPTION OF THE RELATED ART

Derivatives of 3-aryl-3-hydroxy-2-aminopropionic acid amides, 3-heteroaryl-3-hydroxy-2-amino-propionic acid amides and related compounds having analgesic and in some cases immuno stimulant activity have been disclosed in US Patent Publication US 2009-0036436 and in International patent publication WO06/081273. The free base of the present salt, including the various stereoisomeric forms of the free base, viz., (+/−)-erythro-2-amino-3-hydroxy-3-pyridin-4-yl-1-pyrrolidin-1-yl-propan-1-one, (+/−)-threo-2-amino-3-hydroxy-3-pyridin-4-yl-1-pyrrolidin-1-yl-propan-1-one, as well as the dihydrochloride salt of the free base have been disclosed in the above patent publications.

SUMMARY OF THE INVENTION

In one of many embodiments, the present invention is directed to (−)-(2R,3S)-2-amino-3-hydroxy-3-pyridin-4-yl-1-pyrrolidin-1-yl-propan-1-one (L)-(+) tartrate, i.e., the monotartrate salt. Other names for this salt include: DL-threo-2-amino-3-hydroxy-3-(pyridin-4-yl)-1-(pyrrolidin-1-yl)propan-1-one L-(+)-tartrate; (2R,3S)-2-amino-3-hydroxy-3-(pyridin-4-yl)-1-(pyrrolidin-1-yl)propan-1-one 2,3-dihyroxysuccinate; 1-Propanone, 2-amino-3-hydroxy-3-(4-pyridinyl)-1-(1-pyrrolidinyl)-, (2R,3S)-, L-tartrate (1:1) (CA Index Name); and Butanedioic acid, 2,3-dihydroxy-, (2R,3R)-, compound with (2R,3S)-2-amino-3-hydroxy-3-(4-pyridinyl)-1-(1-pyrrolidinyl)-1-propanone (1:1) (IUPAC Name). The structure of this salt can be represented by the formula:

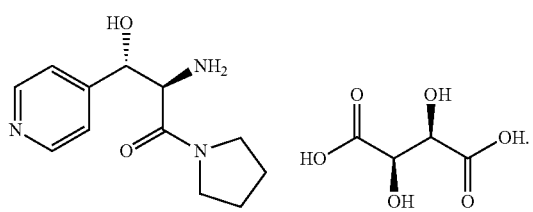

In another embodiment, the salt is a crystalline material.

In another embodiment, the salt exhibits an X-ray powder diffraction spectrum having characteristic peaks expressed in degrees (2θ) at approximately:

| 2θ |
| --- |
| 7.89 |
| 15.13 |
| 15.19 |
| 16.71 |
| 16.83 |
| 24.58. |

In another embodiment, the present invention is directed to a pharmaceutical composition comprising the aforementioned tartrate salt, and at least one pharmaceutically acceptable carrier.

In another embodiment, the present invention is directed to a method of treating pain (such as chronic pain) in a mammal, said method comprising administering to said mammal in need thereof, a therapeutically effective amount of the salt of claim 1.

In another embodiment, the present invention is directed to a process for preparing (−)-(2R,3S)-2-Amino-3-hydroxy-3-pyridin-4-yl-1-pyrrolidin-1-yl-propan-1-one (L)-(+) tartrate salt, said process comprising:

(a) Reacting ethyl isocyanoacetate with pyrrolidine to produce an intermediate 1, which is then reacted with 4-Pyridinecarboxyaldehyde to produce an intermediate 2, wherein intermediate 2 is hydrolyzed to (+/−)-DL-threo-2-amino-3-hydroxy-3-pyridin-4-yl-1-pyrrolidin-1-yl-propan-1-one dihydrochloride;

(b) Resolving the (+/−)-D L-threo-2-amino-3-hydroxy-3-pyridin-4-yl-1-pyrrolidin-1-yl-propan-1-one dihydrochloride in the presence of Di-p-toluoyl-L-tartaric acid to produce (−)-(2R,3S)-2-Amino-3-hydroxy-3-pyridin-4-yl-1-pyrrolidin-1-yl-propan-1-one di-p-toluoyl-L-tartrate;

(c) Converting the (−)-(2R,3S)-2-Amino-3-hydroxy-3-pyridin-4-yl-1-pyrrolidin-1-yl-propan-1-one di-p-toluoyl-L-tartrate in the presence of L-tartaric acid to crude (−)-(2R,3S)-2-Amino-3-hydroxy-3-pyridin-4-yl-1-pyrrolidin-1-yl-propan-1-one (L)-(+) tartrate salt; and (d) Crystallization of the crude (−)-(2R,3S)-2-Amino-3-hydroxy-3-pyridin-4-yl-1-pyrrolidin-1-yl-propan-1-one (L)-(+) tartrate salt in the presence of a suitable solvent to produce purified (−)-(2R,3S)-2-Amino-3-hydroxy-3-pyridin-4-yl-1-pyrrolidin-1-yl-propan-1-one (L)-(+) tartrate salt.

In another embodiment, in step (a) of the above-mentioned process, intermediate 1 is not isolated and is represented by the structure

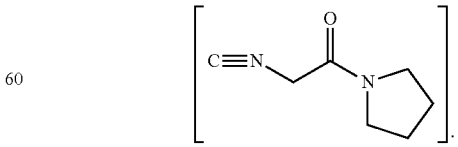

In another embodiment, in step (a) of the above-mentioned process, intermediate 2 is not isolated and is represented by the structure

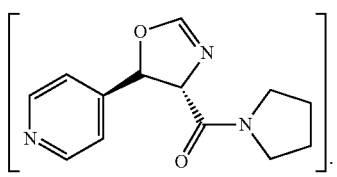

In another embodiment, in step (d) of the above-mentioned process, the suitable solvent comprises methanol.

In another embodiment, the present invention is directed to (−)-(2R,3S)-2-amino-3-hydroxy-3-pyridin-4-yl-1-pyrrolidin-1-yl-propan-1-one (L)-(+) tartrate salt made by the above-mentioned process.

DETAILED DESCRIPTION OF THE INVENTION

Salt Screen Studies

Figure 1:
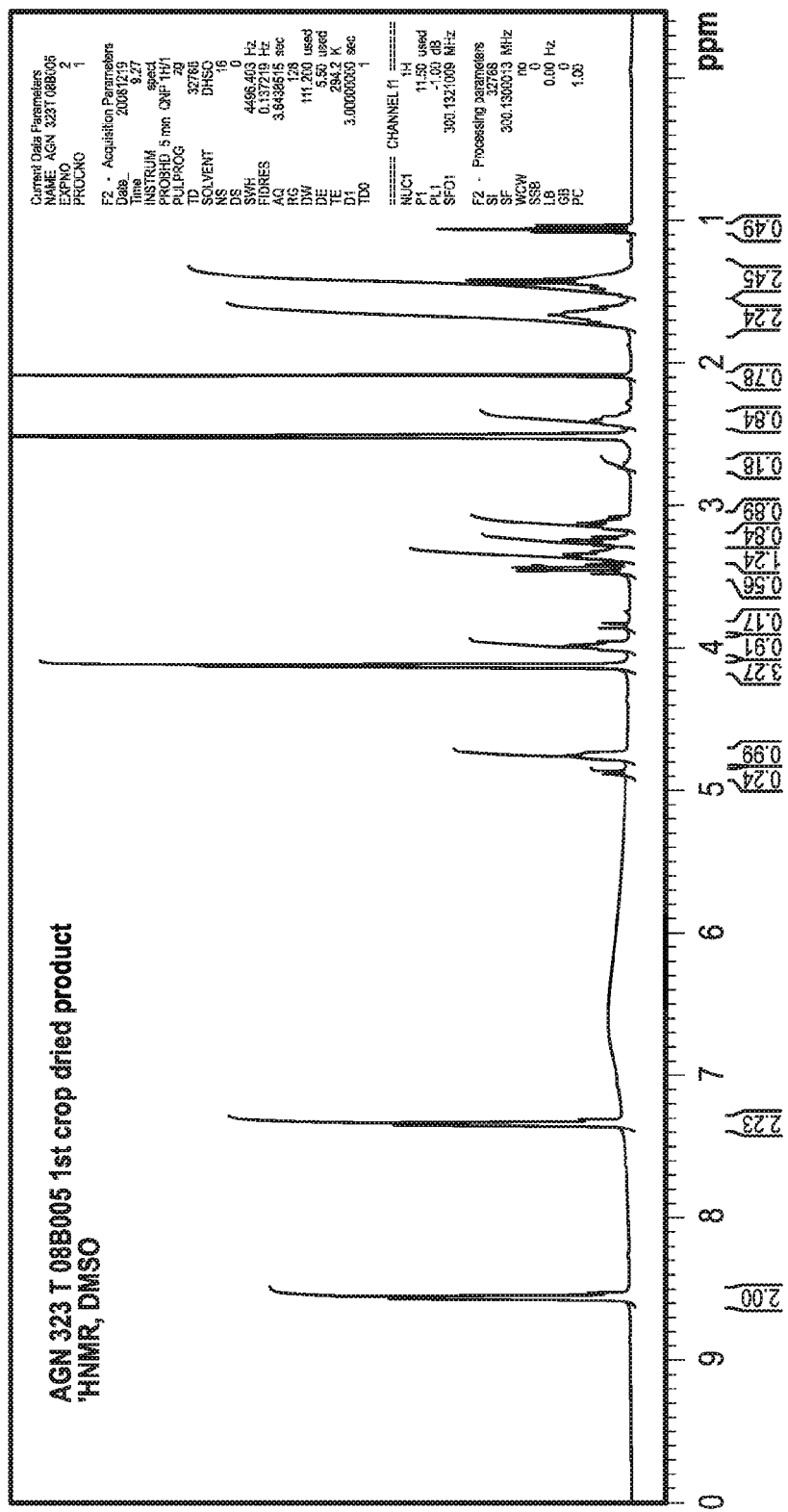
FIG. 1 is a 1H-NMR (dmso-d6) spectrum of crude (−)-(2R,3S)-2-Amino-3-hydroxy-3-pyridin-4-yl-1-pyrrolidin-1-yl-propan-1-one L-(+)tartrate (ON-PYRAMIDE L Tartrate).
Figure 2:
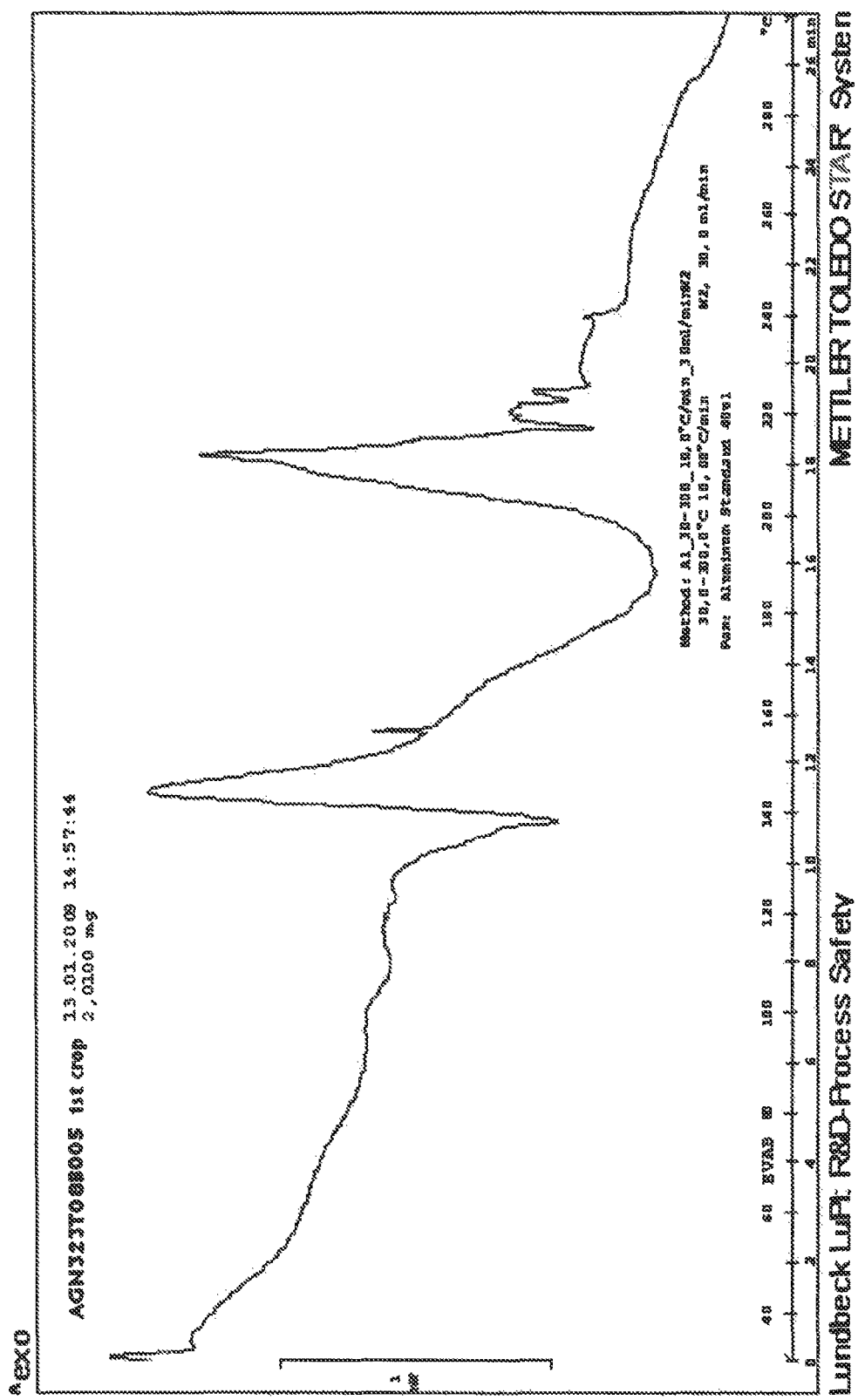
FIG. 2 is a Differential Scanning calorimetry (DSC) spectrum of a $1^{st}$ crop of crude (−)-(2R,3S)-2-Amino-3-hydroxy-3-pyridin-4-yl-1-pyrrolidin-1-yl-propan-1-one L-(+)tartrate (ON-PYRAMIDE L Tartrate).
Figure 3A:
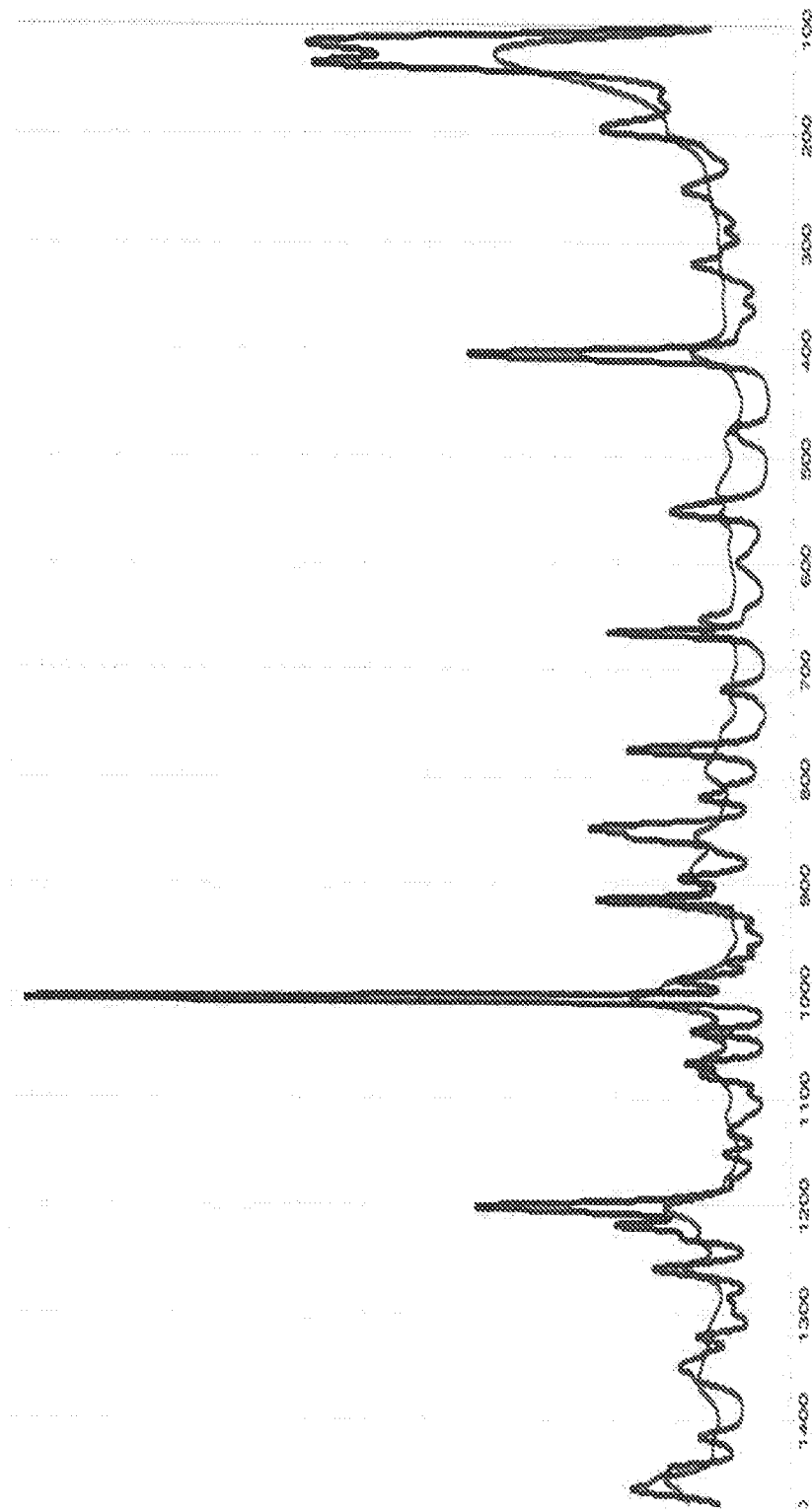
FIGS. 3A and 3B shows superimposed Raman spectra of a crude ($1^{st}$ crop) of (−)-(2R,3S)-2-Amino-3-hydroxy-3-pyridin-4-yl-1-pyrrolidin-1-yl-propan-1-one L-(+)tartrate and a standard recrystallized sample.
Figure 3B:
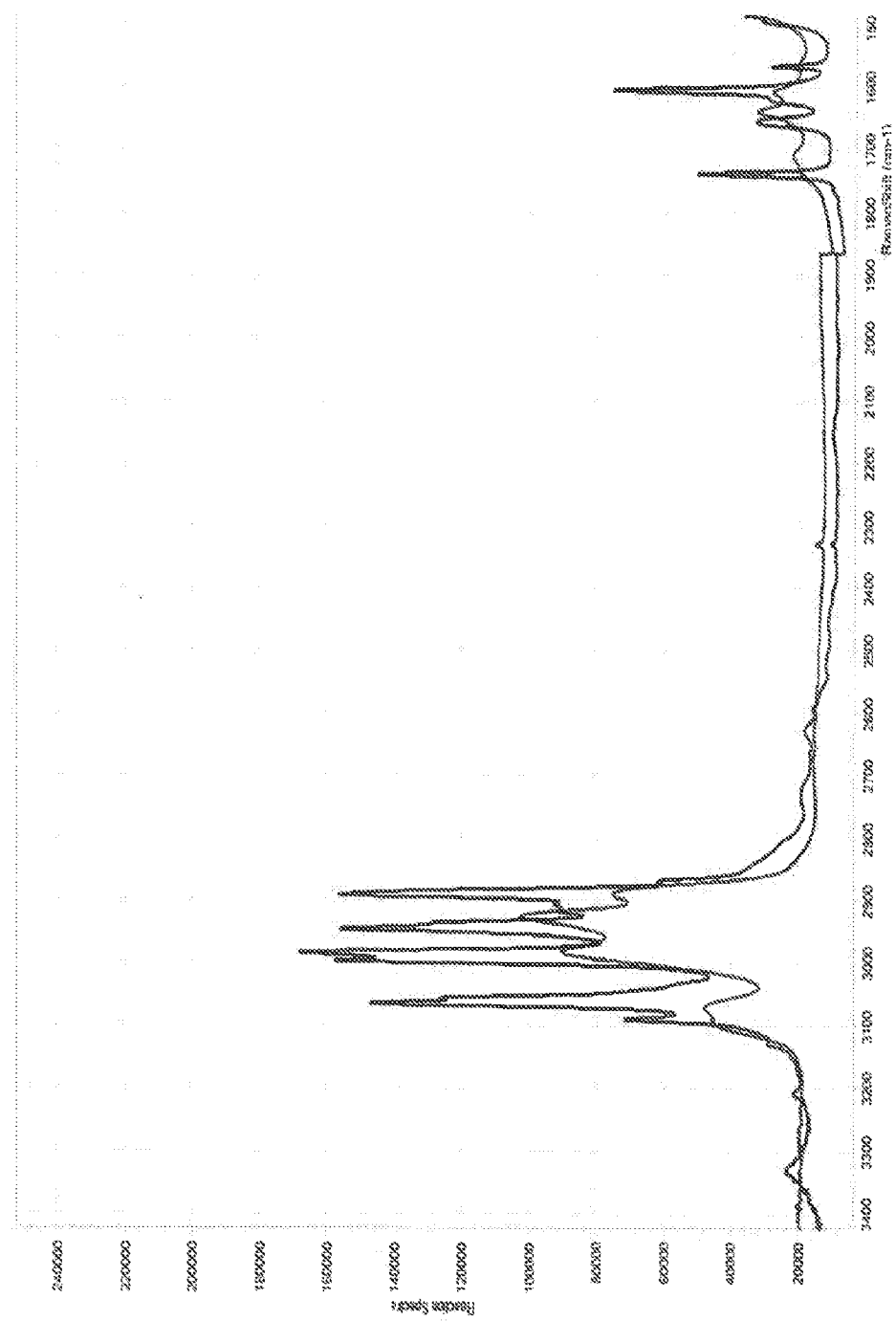
Figure 4:
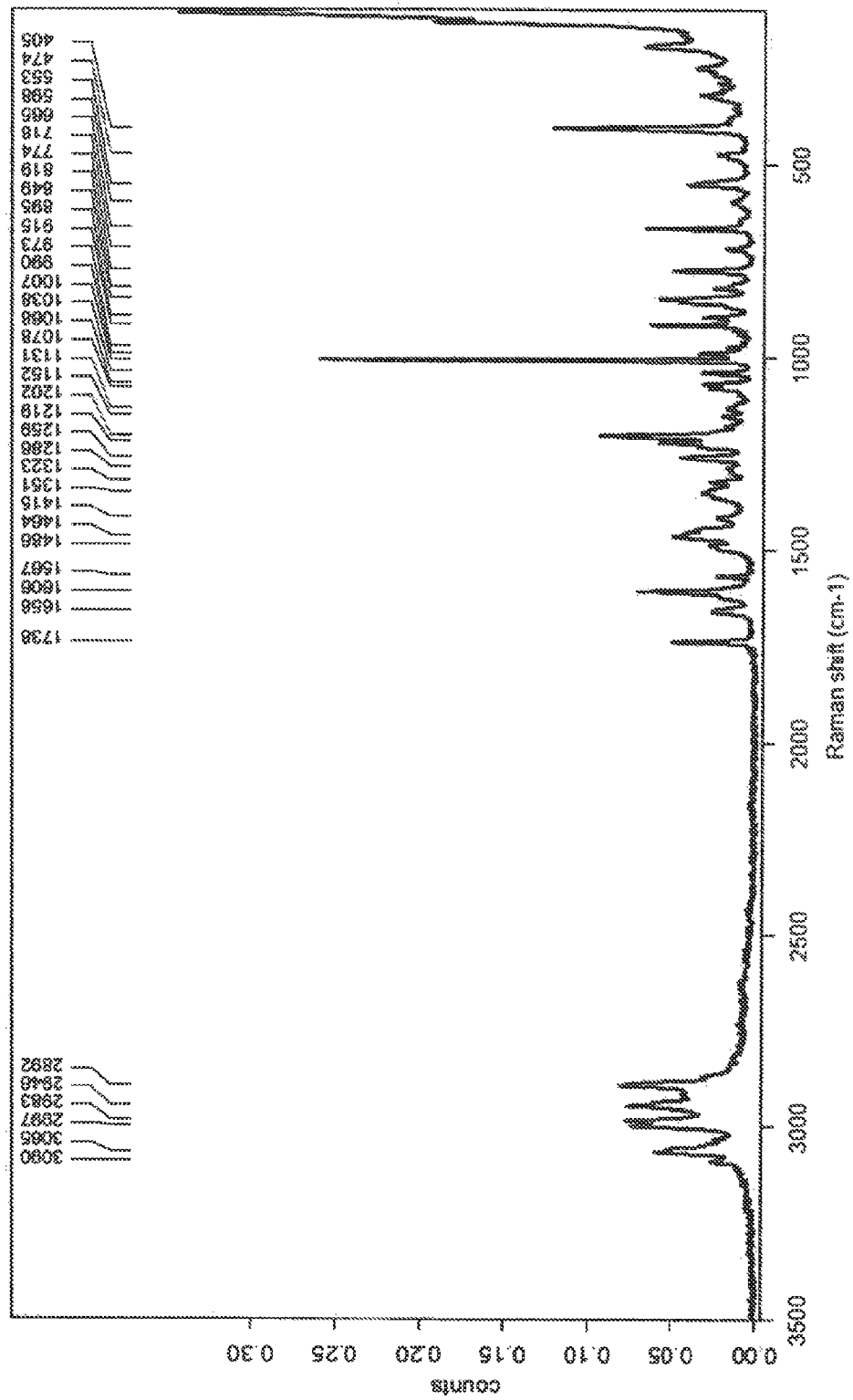
FIG. 4 shows Raman spectrum of a purified sample of (−)-(2R,3S)-2-Amino-3-hydroxy-3-pyridin-4-yl-1-pyrrolidin-1-yl-propan-1-one L-(+)tartrate. The sample is crystalline and corresponds to form A.
Figure 5:
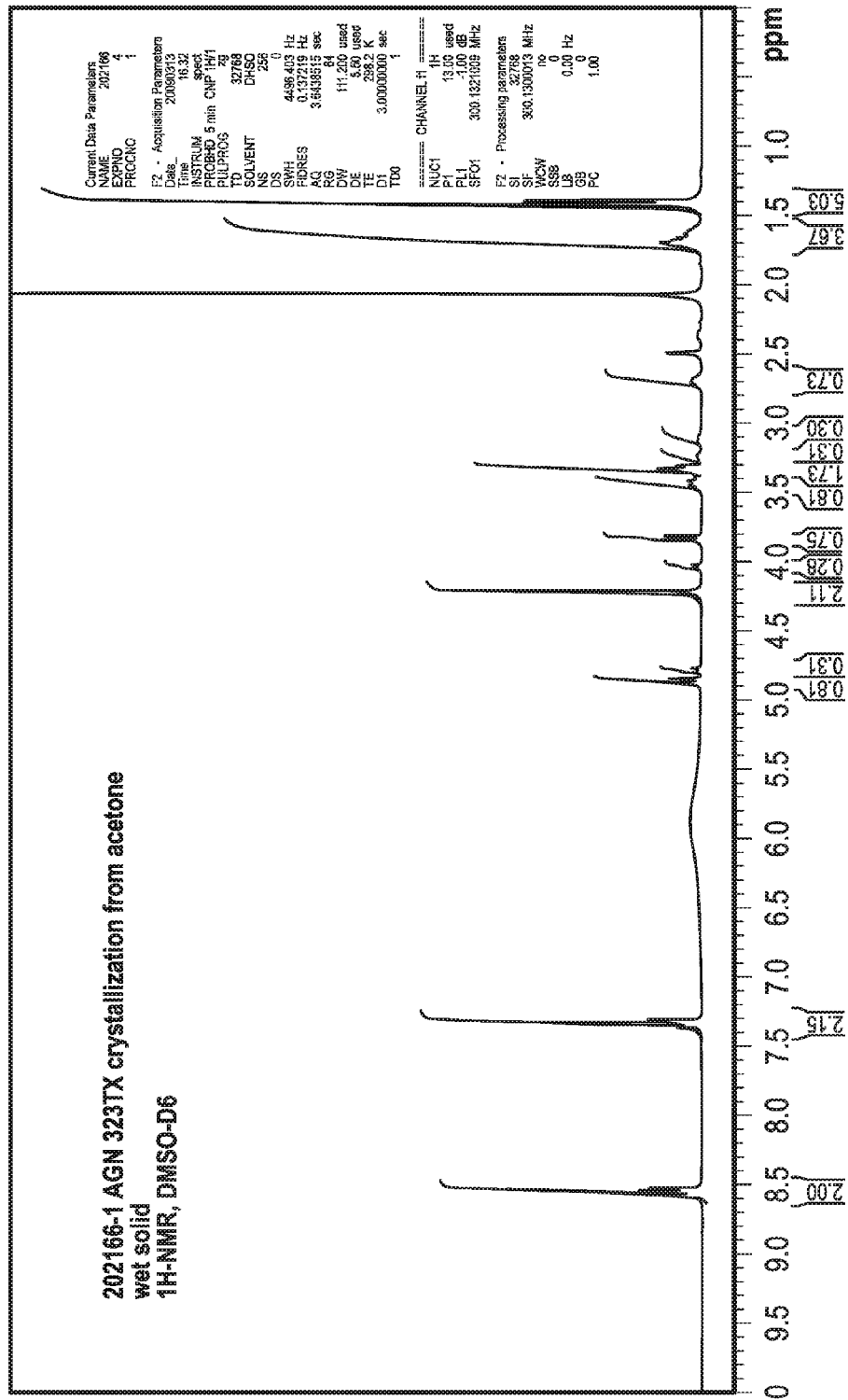
FIG. 5 shows a $^1$H-NMR (dmso-d6) spectrum of a recrystallized (from acetone) sample of (−)-(2R,3S)-2-Amino-3-hydroxy-3-pyridin-4-yl-1-pyrrolidin-1-yl-propan-1-one L-tartrate.

Initial salt screen study was performed on the racemic mixture. The following counterions were used: sulfuric acid, glutamic acid, hydrochloric acid, phosphoric acid, maleic acid, aspartic acid, naphthalene-2-sulfonic acid, naphthalene-1,5-disulfonic acid, benzenesulfonic acid, ethane-1,2-disulfonic acid, ethanesulfonic acid, methanesulfonic acid, p-toluenesulfonic acid, palmoic acid, dichloroacetic acid, and (+)-camphor-10-sulfonic acid. From these, the p-toluenesulfonate and the maleate salts were found to be most successful. However neither of these salts turned out to be acceptable. It is advisable to avoid sulfonates because of the potential presence of sulfonate esters, potent teratogens. Maleates may cause renal problems, especially in high doses.

In another salt from optimization study for the dibasic drug molecule (+/−)-erythro-2-amino-3-hydroxy-3-pyridin-4-yl-1-pyrrolidin-1-yl-propan-1-one, the dihydrochloride was the first salt prepared and characterized. It was found to be hygroscopic and not well suited for development (although it can be easily handled in the isolation on large scale). The following counterions were used: sulfuric acid, 1-hydroxy-2-naphthoic acid, methanesulfonic acid, naphthalene-2-sulfonic acid, benzenesulfonic acid, (L-) glutamic acid, malonic acid, citric acid, (−)-L-malic acid, lactic acid, ascorbic acid, and acetic acid. Of these the pursuance of mono-acetate, the naphthalene-2-sulfonate and the 1-hydroxy-2-naphthoate salts were recommended. However, both the acetate and the naphthalene-2-sulfonate showed unsuitable behavior: the acetate salt deliquesced at 51% RH, and the naphthalene-2-sulfonate was difficult to scale up.

The latter salt also represented a large counterion compared to the base and, especially at high doses, this was perceived as a definite disadvantage.

In a third salt screening study, the following counterions were used: acetic acid, L-Aspartic acid, benzoic acid, citric acid, D-gluconic acid, D-glucuronic acid, hippuric acid, hydrochloric acid, (−)-L malic acid, (+)-L-lactic acid, maleic acid, L-malic acid, (+)-L-mandelic acid, 1-hydroxy-2-naphthoic acid, oleic acid, palmitic acid, pamoic acid, phosphoric acid, saccharin, stearic acid, succinic acid, sulfuric acid. Of these, two salts, the L-mandelate and the stearate showed the most promising physicochemical properties. The L-mandelate salt was seriously considered for development, however, this study was halted considering potential toxicological issues. After weighing all the information (stability, toxicity consideration, etc.) it was decided that the L-tartrate salt (i.e., mono-L-tartrate) would be the best candidate for further development.

Preparation of (−)-(2R,3S)-2-amino-3-hydroxy-3-pyridin-4-yl-1-pyrrolidin-1-yl-propan-1-one (L)-(+) tartrate salt This salt is made in four steps from commercially available starting materials. The first step is the synthesis of racemic hydrochloride salt, i.e., (+/−)-DL-threo-2-amino-3-hydroxy-3-pyridin-4-yl-1-pyrrolidin-1-yl-propan-1-one dihydrochloride, and is shown schematically below:

Step 1: Synthesis of (+/−)-DL-threo-2-amino-3-hydroxy-3-pyridin-4-yl-1-pyrrolidin-1-yl-propan-1-one di hydrochloride form is isolated and purified by crystallization to give pure (+/−)-DL-threo-2-amino-3-hydroxy-3-pyridin-4-yl-1-pyrrolidin-1-yl-propan-1-one dihydrochloride. The detailed manufacturing process is given below:

Charge a reactor with 65 Kg (76 Lt) of Pyrrolidine, 220 Kg of MeOH (278 Lt), start stirring and set the temperature at T=5-20° C. Add slowly, in about 5 hours, under stirring, 100 Kg of Ethyl isocyanoacetate, by maintaining the temperature at T=5-20° C. Maintain the reaction mixture at T=5-20° C. for at least 2 hours, then cool down to T=−13 to −7° C., and dilute with 300 Kg (226 Lt) CH$_2$Cl$_2$ Add slowly to the obtained solution 100 Kg (88 Lt) 4-Pyridinecarboxaldehyde by maintaining the temperature at T=13-0° C. Keep the reaction mixture at T=−5÷0° C. for at least 1 hour.

Charge a second stainless steel reactor with 61 Kg KOH, 800 Kg (602 Lt) CH$_2$Cl$_2$; cool down the mixture, under stirring to T=−13 to −7° C. Transfer the reaction mixture from the glass line reactor to the stainless steel reactor, containing the KOH solution under stirring, by maintaining the temperature at T=−5-0° C. Maintain the reaction mixture at T=−5-0° C. for at least 4 hours; then add slowly, under stirring, 500 Kg H$_2$O, by maintaining the temperature at T=−5-0° C. Set the temperature of the mixture at T=0-5° C. and maintain under stirring for about 0.5 hours. Stop the stirring and leave the phases to separate for at least 0.5 hours.

Transfer the organic phase into the glass lined reactor. Add to the aqueous phase 600 Kg (450 Lt) CH$_2$Cl$_2$ and keep under stirring for about 0.5 hours at T=0-5° C.

Stop the stirring and leave the phases to separate for at least 0.5 hours. Transfer the organic phase to the glass lined reactor containing the first organic phase. Charge the glass

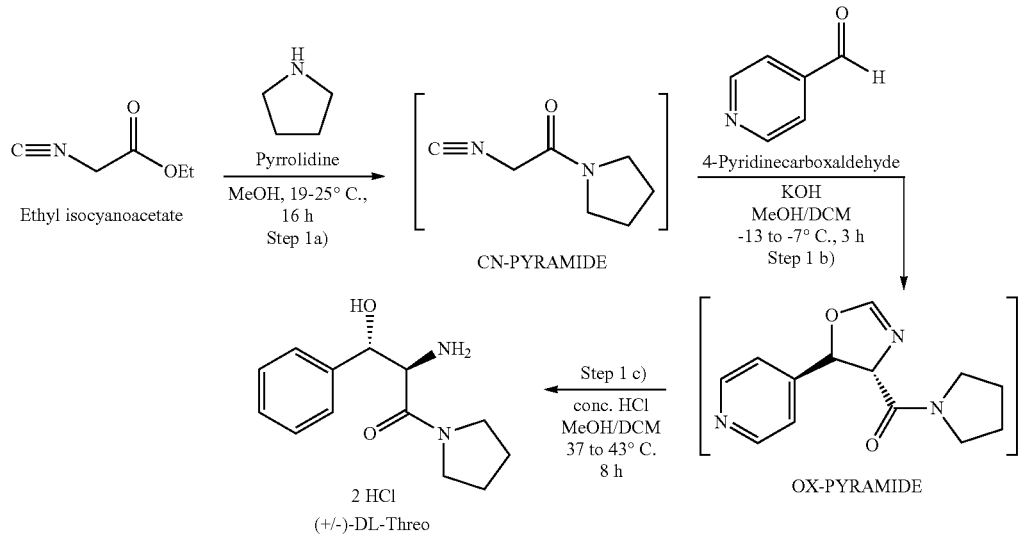

lined reactor, containing the combined organic phases, with 500 Kg H$_2$O. Set the temperature of the mixture at T=0-5° C. and maintain under stirring for about 0.5 hours. Stop the stirring and leave the phases to separate for at least 0.5 hours.

Store the organic phase in a reactor. Add slowly, under stirring, to the organic phase 37% 195 Kg (162 Lt) aqueous HCl. During the addition let the temperature rise to T$_{max}$≤35° C. Add under stirring, by maintaining the temperature at T≤35° C., 700 Kg (886 Lt) MeOH. Heat to reflux Pyrrolidine and ethyl isocyanoacetate are first reacted to form an intermediate 1 (CN-Pyramide) which is not isolated. This material is then reacted with 4-pyridinecarboxaldehyde to form a dihydro-oxazol intermediate, intermediate 2 (Ox-Pyramide) which is not isolated. The diastereomeric threo configuration of the drug substance is determined in this step of the process. The dihydro-oxazol is hydrolyzed to form the racemic threo-2-amino-3-hydroxy compound. The erythro-2-amino-3-hydroxy impurity can be formed as a by-product during this transformation. The dihydrochloride salt threo- (T=37-43° C.), under stirring and maintain for at least 9 hours. Concentrate the mixture to residue, via atmospheric distillation $T_{max}$=45° C. Cool down to T=30° C. and add 1000 Kg (1250 Lt) denatured EtOH. Concentrate the mixture to about 380-420 Kg residual, by distilling at atmospheric pressure at $T_{max}$=45° C. Cool down to T=30° C. and add 1398 Kg (1766 Lt) of denatured EtOH; then cool down the mixture to T=−3-3° C. and maintain under stirring at that temperature for at least 3 hours.

Centrifuge the crystalline precipitate and wash the cake with 441 Kg (561 Lt) of denatured EtOH. 170-300 Kg of wet (+/−)-DL-threo-2-amino-3-hydroxy-3-pyridin-4-yl-1-pyrrolidin-1-yl-propan-1-one dihydrochloride are expected. Dry the obtained product under vacuum at $T_{max}$=40° C. for at least 12 hours. 145-250 Kg of (+/−)-DL-threo-2-amino-3-hydroxy-3-pyridin-4-yl-1-pyrrolidin-1-yl-propan-1-one dihydrochloride are expected. The molar % yield varies from about 51% to about 80%, average 70%.

Step 2. Synthesis of (−)-(2R,3S)-2-Amino-3-hydroxy-3-pyridin-4-yl-1-pyrrolidin-1-vi-propan-1-one di-p-toluoyl-L-tartrate

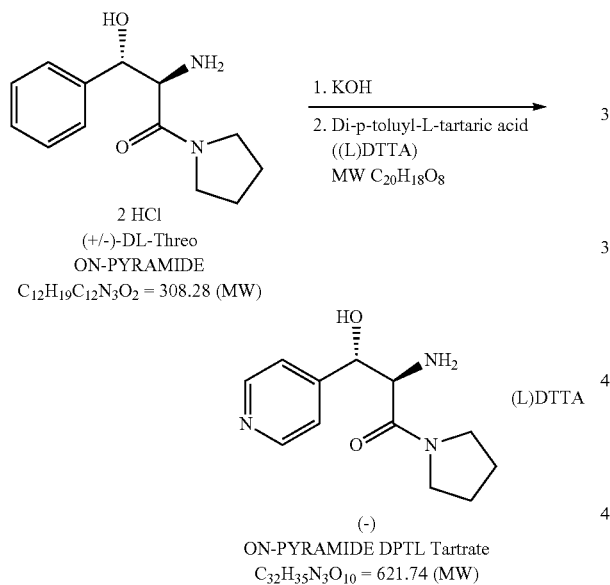

(+/−)-DL-threo-2-amino-3-hydroxy-3-pyridin-4-yl-1-pyrrolidin-1-yl-propan-1-one dihydrochloride is resolved, in the second step, into its chiral enantiomers by chemical resolution using commercially available di-p-toluoyl-L-tartaric acid (L-DTTA), giving the resolved, chiral, (−)-(2R,3S)-2-Amino-3-hydroxy-3-pyridin-4-yl-1-pyrrolidin-1-yl-propan-1-one di-p-toluoyl-L-tartrate. The detailed manufacturing process is given below:

Charge a reactor with 75 Kg KOH and 993 Kg (1265 Lt) MeOH; stir and set the temperature to T=20-30° C. Dissolve in another reactor 200 Kg of (+/−)-DL-threo-2-amino-3-hydroxy-3-pyridin-4-yl-1-pyrrolidin-1-yl-propan-1-one dihydrochloride with 198 Kg (249 Lt) MeOH at T=20-30° C. under stirring for about 20-40 minutes, then cool down the solution to T=8-10° C. Add slowly the methanolic solution of KOH, under stirring, by maintaining the temperature at T=8-10° C. Heat up the mixture, under stirring to T=20-25° C. and maintain for 2.5-3.5 hours. Charge another reactor with 1073 Kg (807 Lt) $CH_2Cl_2$, 240 Kg of di-p-toluyl L-tartaric acid and 80 Kg (101 Lt) of MeOH, stirring at T=20-25° C. until complete dissolution. Centrifuge the inorganic salts obtained from the reaction of (+/−)-DL-threo-2-amino-3-hydroxy-3-pyridin-4-yl-1-pyrrolidin-1-yl-propan-1-one dihydrochloride and KOH and wash the cake with 158 Kg (200 Lt) of methanol. Transfer the organic solution filtering through a 0.65 μm cartridge, in about 3-4 hours, into the glass lined reactor containing the di-p-toluyl L-tartaric acid solution, by maintaining the temperature at T=20-25° C. Keep under stirring the suspension, at T=20-25° C., for at least 14 hours. Centrifuge the crystalline solid and wash the cake with 536 Kg (680 Lt) of MeOH. 250-350 Kg of wet (−)-(2R,3S)-2-Amino-3-hydroxy-3-pyridin-4-yl-1-pyrrolidin-1-yl-propan-1-one di-p-toluoyl-L-tartrate (ON-PYRAMIDE DPTL tartrate) expected. Dry the obtained product under vacuum at $T_{max}$=40° C. for at least 12 hours. 168-280 Kg of (−)-(2R,3S)-2-Amino-3-hydroxy-3-pyridin-4-yl-1-pyrrolidin-1-yl-propan-1-one di-p-toluoyl-L-tartrate are expected. The molar % yield varies from about 84% to about 100%.

Step 3. Synthesis of crude (−)-(2R,3S)-2-Amino-3-hydroxy-3-pyridin-4-yl-1-pyrrolidin-1-yl-propan-1-one L-tartrate (ON-PYRAMIDE L Tartrate)

Step 3a: Free Base Formation

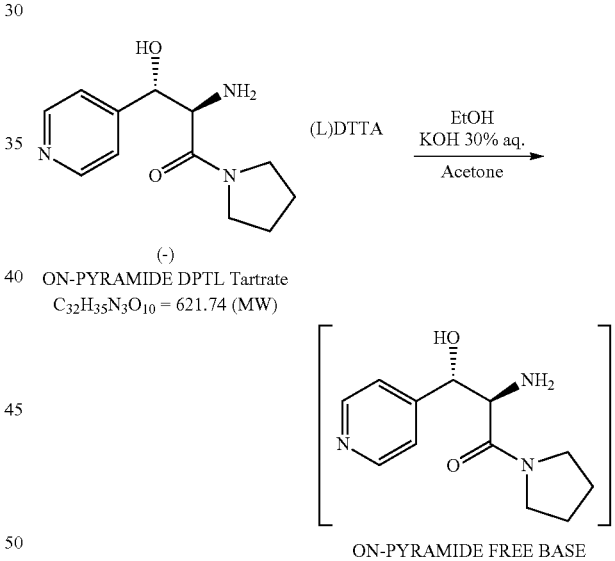

Step 3b: Resin Treatment

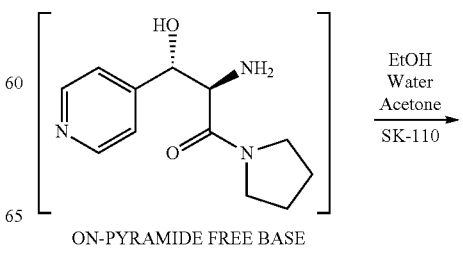

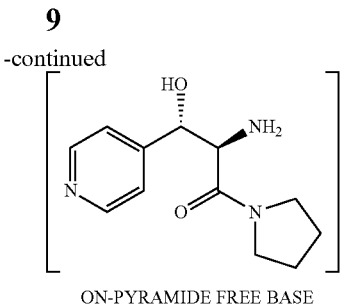

ON-PYRAMIDE FREE BASE

Step 3c: Tartrate formation

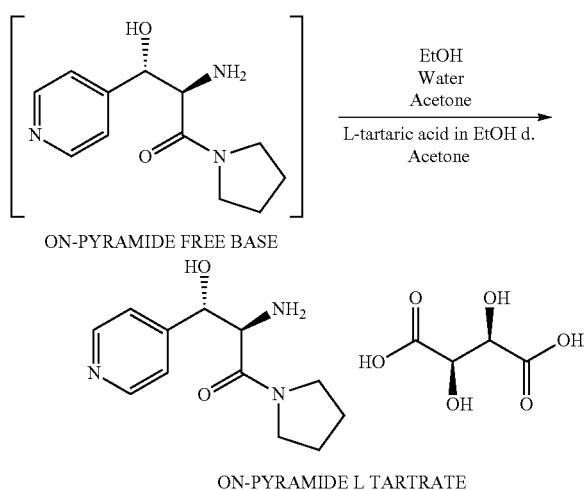

ON-PYRAMIDE L TARTRATE

In the third step, (−)-(2R,3S)-2-Amino-3-hydroxy-3-pyridin-4-yl-1-pyrrolidin-1-yl-propan-1-one di-p-toluoyl-L-tartrate is converted to the corresponding crude L-tartrate salt, i.e. crude (−)-(2R,3S)-2-Amino-3-hydroxy-3-pyridin-4-yl-1-pyrrolidin-1-yl-propan-1-one L-tartrate (ON-PYRAMIDE L Tartrate).

Step 3 contains three sub-steps. In step 3a, the (−)-(2R,3S)-2-Amino-3-hydroxy-3-pyridin-4-yl-1-pyrrolidin-1-yl-propan-1-one di-p-toluoyl-L-tartrate (ON-PYRAMIDE DPTL Tartrate) is treated with aqueous KOH/Ethanol and acetone to give the corresponding free base, i.e., (−)-(2R,3S)-2-Amino-3-hydroxy-3-pyridin-4-yl-1-pyrrolidin-1-yl-propan-1-one (ON-PYRAMID free base). Following this, there is a resin treatment with a sulfonic resin. Finally, tartrate formation takes place by treatment of the free base with L-tartaric acid in the presence of denatured ethanol. The detailed manufacturing process is given below:

Charge a stainless steel reactor with 200 Kg of (−)-(2R,3S)-2-Amino-3-hydroxy-3-pyridin-4-yl-1-pyrrolidin-1-yl-propan-1-one di-p-toluoyl-L-tartrate (ON-PYRAMIDE DPTL Tartrate), 790 Kg (1000 Lt) acetone, and 395 Kg (500 Lt) EtOH. Stir and cool down the mixture to T=7-9° C. Dissolve in another vessel, 40 Kg KOH and 100 Lt water. Add the KOH solution to the reaction mixture in 4-6 hours, under vigorous stirring, by maintaining the temperature at T=7-9° C. Add, under vigorous stirring, 790 Kg (1000 Lt) acetone by maintaining the temperature at T=7-9° C., and keep the mixture under stirring at T=7-9° C. for at least 8 hours. Centrifuge the obtained salts at T=7-9° C. and wash the cake with 158 Kg (200 Lt) of acetone.

Combine the organic solutions. Charge a glass lined reactor with 30 Kg of an acidic sulfonic resin such as Diaion SK110H. Transfer the combined organic solutions into the glass lined reactor containing the sulfonic resin through a 0.65 μm cartridge. Heat up the mixture to 20÷25° C., and stir for at least 2 hours. Filter off the resins with a suitable filter. Wash the lines and the resins with Acetone 158 Kg (200 Lt). Combine and weigh the organic solutions (P (Kg)). Calculate the assay M of (−)-(2R,3S)-2-Amino-3-hydroxy-3-pyridin-4-yl-1-pyrrolidin-1-yl-propan-1-one free base via potentiometric titration.

Charge a stainless steel reactor with S Kg of L-Tartaric acid (where its amount S is calculated by the formula S=[(M*P/100)/325.3*150.09*1.2], and 395 Kg (500 Lt) of denatured EtOH. Set the temperature at T=20-25° C. and stir until complete dissolution. Once the complete dissolution is obtained transfer the L-Tartaric acid solution into a glass lined reactor through a 0.65 μm cartridge. Add slowly, in 5-6 hours, under stirring, the free base solution, filtered through a 0.65 μm cartridge, into the L-Tartaric acid solution, by maintaining the temperature at T=20-25°. Maintain under stirring at T=20-25° C. for 2-2.5 hours.

Add, under stirring, 632 Kg (800 Lt) of acetone and maintain the mixture under stirring for 2-2.5 hours. Cool down the mixture, under stirring, to T=0-5° C. and keep under stirring at that temperature for at least 8 hours. Centrifuge the crystalline solid at T=0-5° C. and wash the cake with 80 Kg (100 Lt) of acetone. 90-140 Kg of wet (−)-(2R,3S)-2-Amino-3-hydroxy-3-pyridin-4-yl-1-pyrrolidin-1-yl-propan-1-one L-tartrate (ON-PYRAMIDE L Tartrate) are expected. Dry the obtained product under vacuum at $T_{max}$=45° C. for at least 12 hours. 70-110 Kg of dry crude (−)-(2R,3S)-2-Amino-3-hydroxy-3-pyridin-4-yl-1-pyrrolidin-1-yl-propan-1-one L-tartrate (ON-PYRAMIDE L Tartrate) are expected. The molar % yield of crude ON-PYRAMIDE L Tartrate varies from about 65% to about 91%.

Step 4. Synthesis of purified (−)-(2R,3S)-2-Amino-3-hydroxy-3-pyridin-4-yl-1-pyrrolidin-1-yl-propan-1-one L-tartrate (ON-PYRAMIDE L Tartrate)

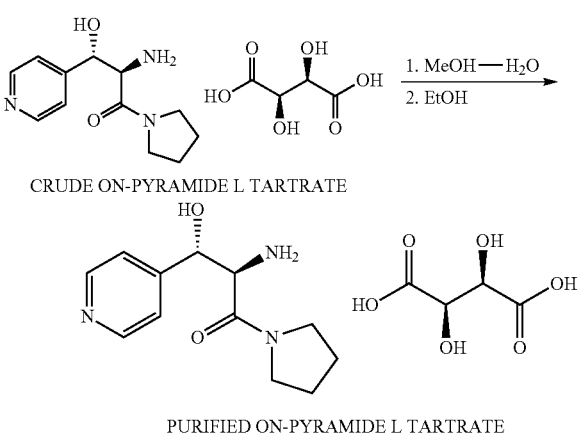

CRUDE ON-PYRAMIDE L TARTRATE

PURIFIED ON-PYRAMIDE L TARTRATE

The crude L-tartrate salt of (−)-(2R,3S)-2-Amino-3-hydroxy-3-pyridin-4-yl-1-pyrrolidin-1-yl-propan-1-one is purified in the fourth step. The detailed manufacturing process is given below:

Charge a reactor with 19 Kg of crude (−)-(2R,3S)-2-Amino-3-hydroxy-3-pyridin-4-yl-1-pyrrolidin-1-yl-propan-1-one L-tartrate (ON-PYRAMIDE L Tartrate), 9.5 Kg $H_2O$, 15 Kg (19 Lt) MeOH by maintaining the temperature at T=18-22° C. Keep under stirring at T=18-22° C. for about 0.5 hours until complete dissolution, check. Add, slowly, under stirring, at T=18÷22° C. MeOH 60 Kg (76 Lt). Maintain under stirring at the same temp for about 15 minutes then seed with 0.01 Kg of pure/purified (−)-(2R,3S)-2-Amino-3-hydroxy-3-pyridin-4-yl-1-pyrrolidin-1-yl-propan-1-one L-tartrate (ON-PYRAMIDE L Tartrate).

Stir for 1 hour at T=18-22° C. then add, slowly EtOH 75 Kg (95 Lt). Cool down the mixture to T=0-5° C. in about 4 hours and maintain at the same temperature under stirring for at least 4 hours. Centrifuge the crystalline product at T=0-5° C. and wash the cake with MeOH 14.4 Kg (18 Lt). Dry the obtained product under vacuum (P=−0.8±0.2 bar) at Tmax=50° C. for at least 12 hours. Sample 2 g of the compound for IPC (Limit: LOD 0.5%). 15-18 Kg of purified (−)-(2R,3S)-2-Amino-3-hydroxy-3-pyridin-4-yl-1-pyrrolidin-1-yl-propan-1-one L-tartrate (ON-PYRAMIDE L Tartrate) are expected. The molar % yield of purified/pure ON-PYRAMIDE L Tartrate varies from about 63% to about 96%, average 85-90%.

Polymorphism Study

Figure 12:
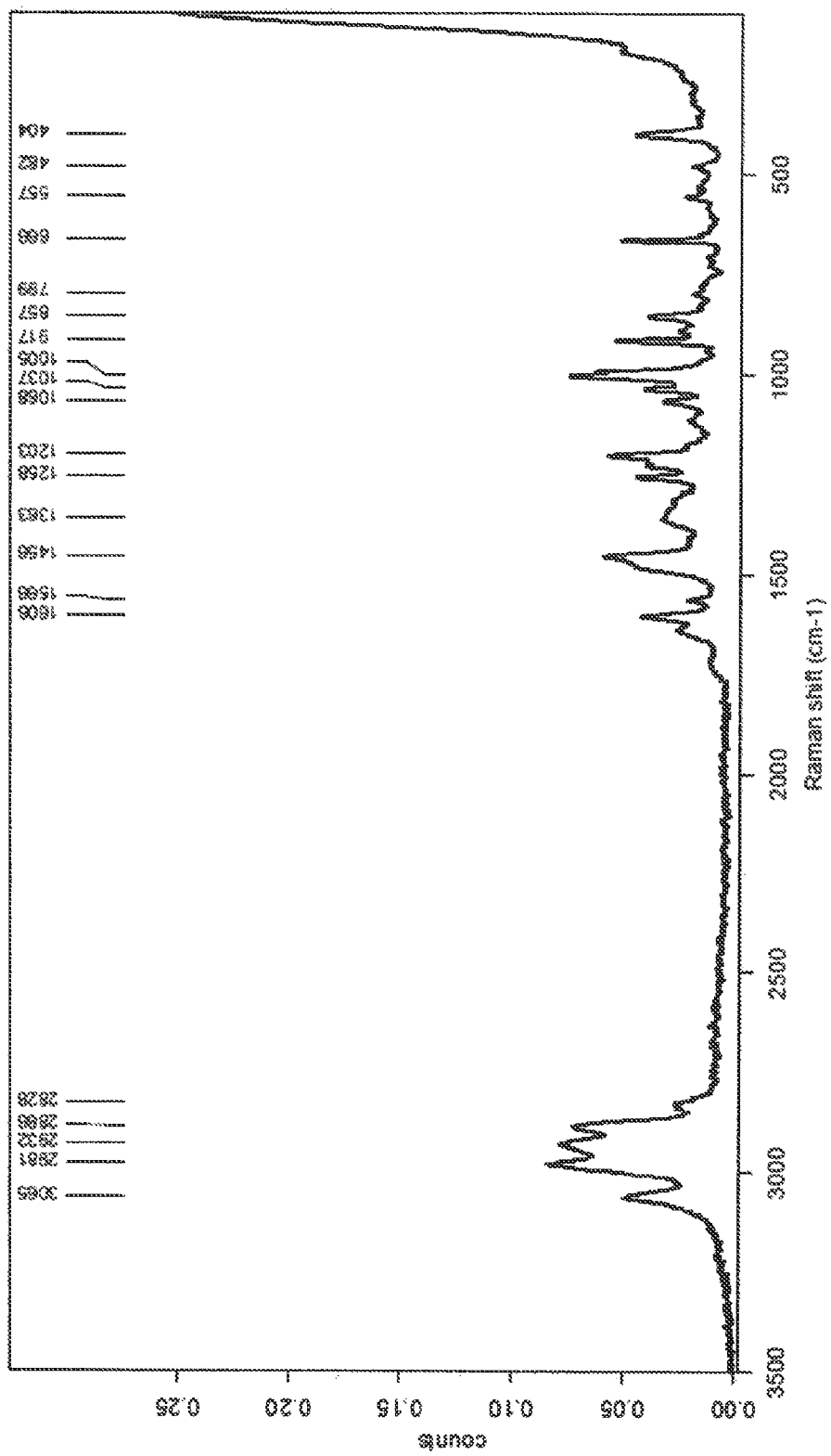
FIG. 12 shows the Raman spectrum of an amorphous sample of (−)-(2R,3S)-2-Amino-3-hydroxy-3-pyridin-4-yl-1-pyrrolidin-1-yl-propan-1-one-L-(+) tartrate. The spectrum is different from that of the crystalline form (form A).
Figure 13:
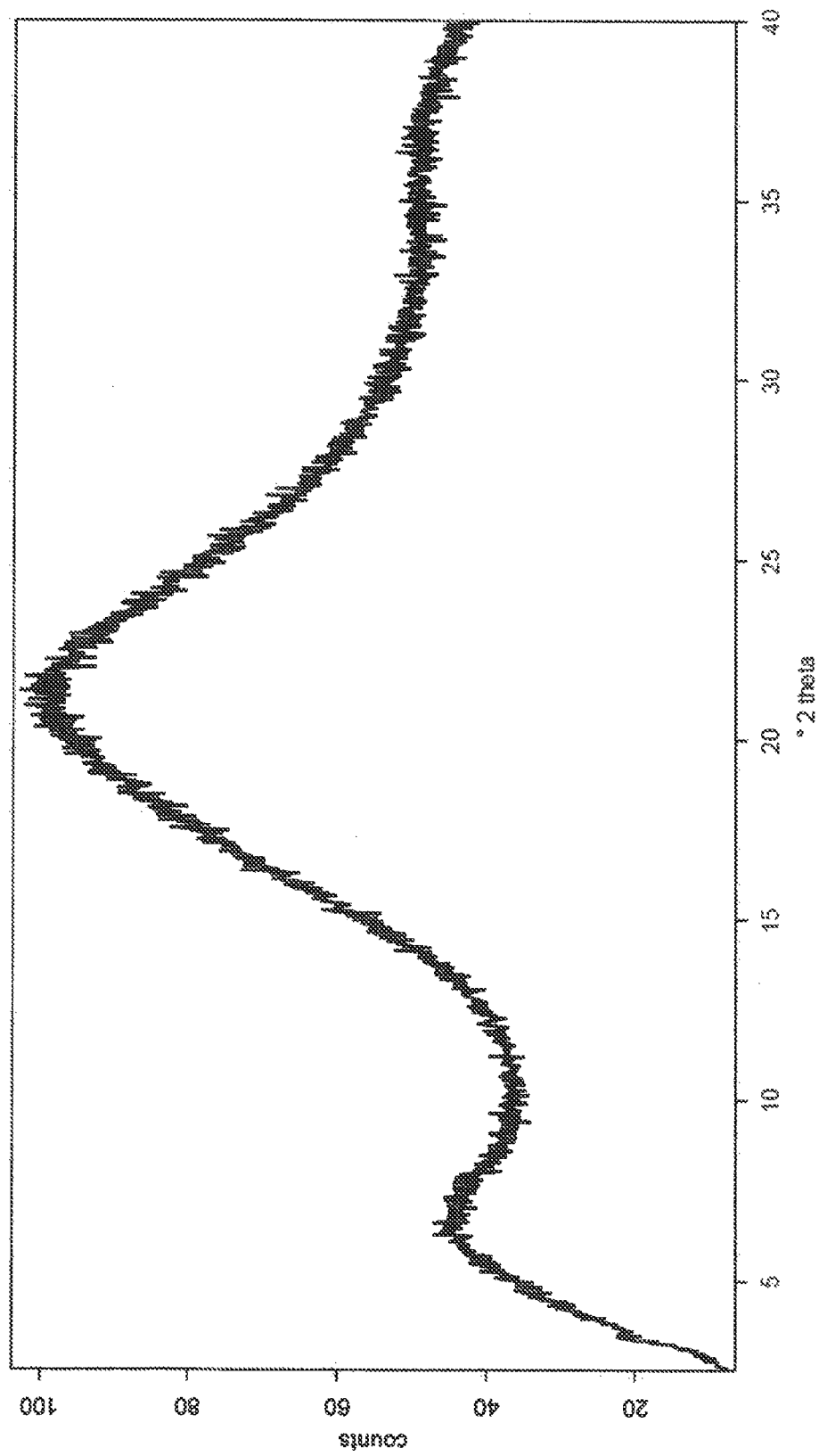
FIG. 13 shows the PXRD pattern of an amorphous sample of (−)-(2R,3S)-2-Amino-3-hydroxy-3-pyridin-4-yl-1-pyrrolidin-1-yl-propan-1-one-L-(+) tartrate.
Figure 14:
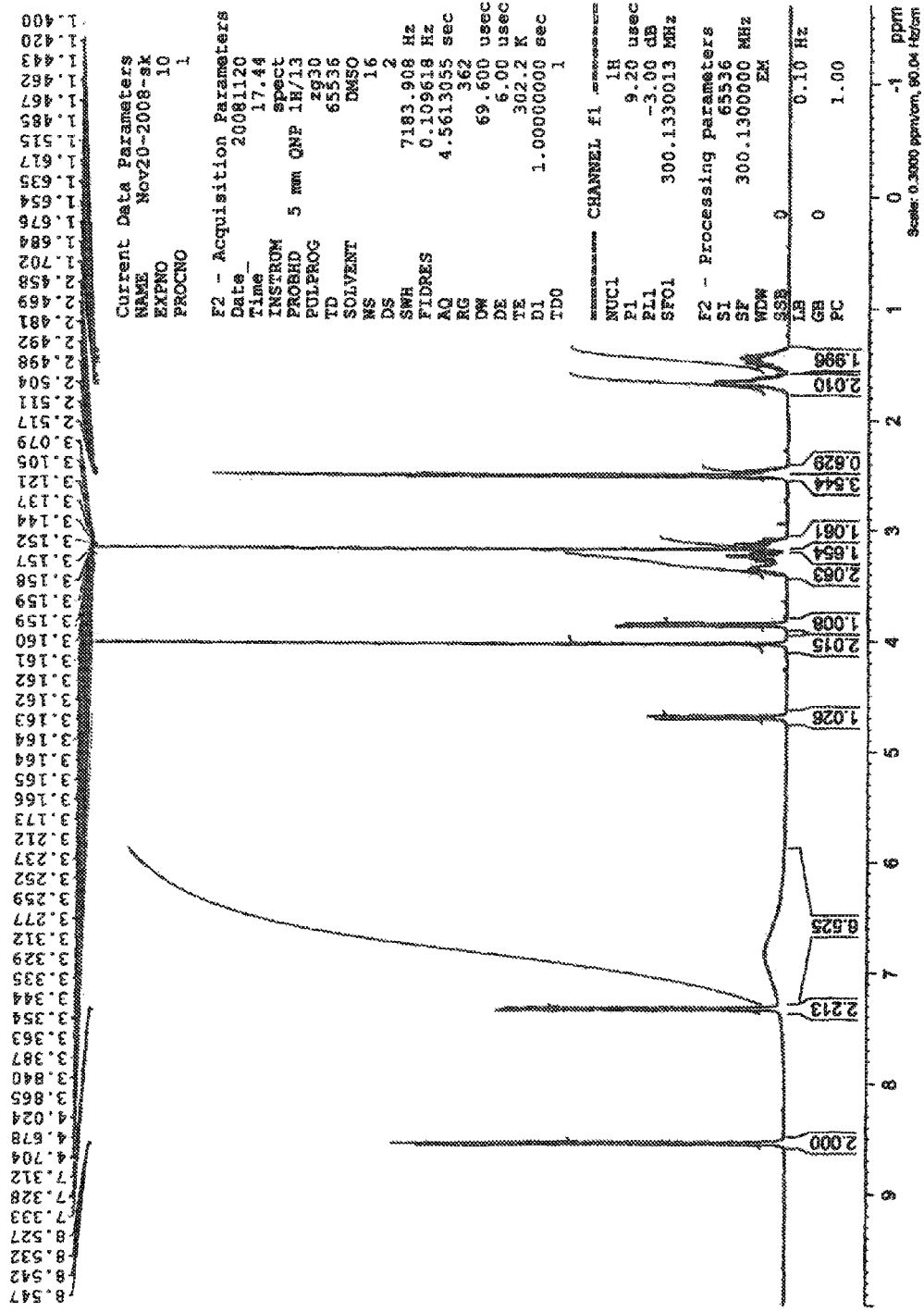
FIG. 14 shows a $^1$H-NMR spectrum of an amorphous sample of (−)-(2R,3S)-2-Amino-3-hydroxy-3-pyridin-4-yl-1-pyrrolidin-1-yl-propan-1-one-L-(+) tartrate.
Figure 15:
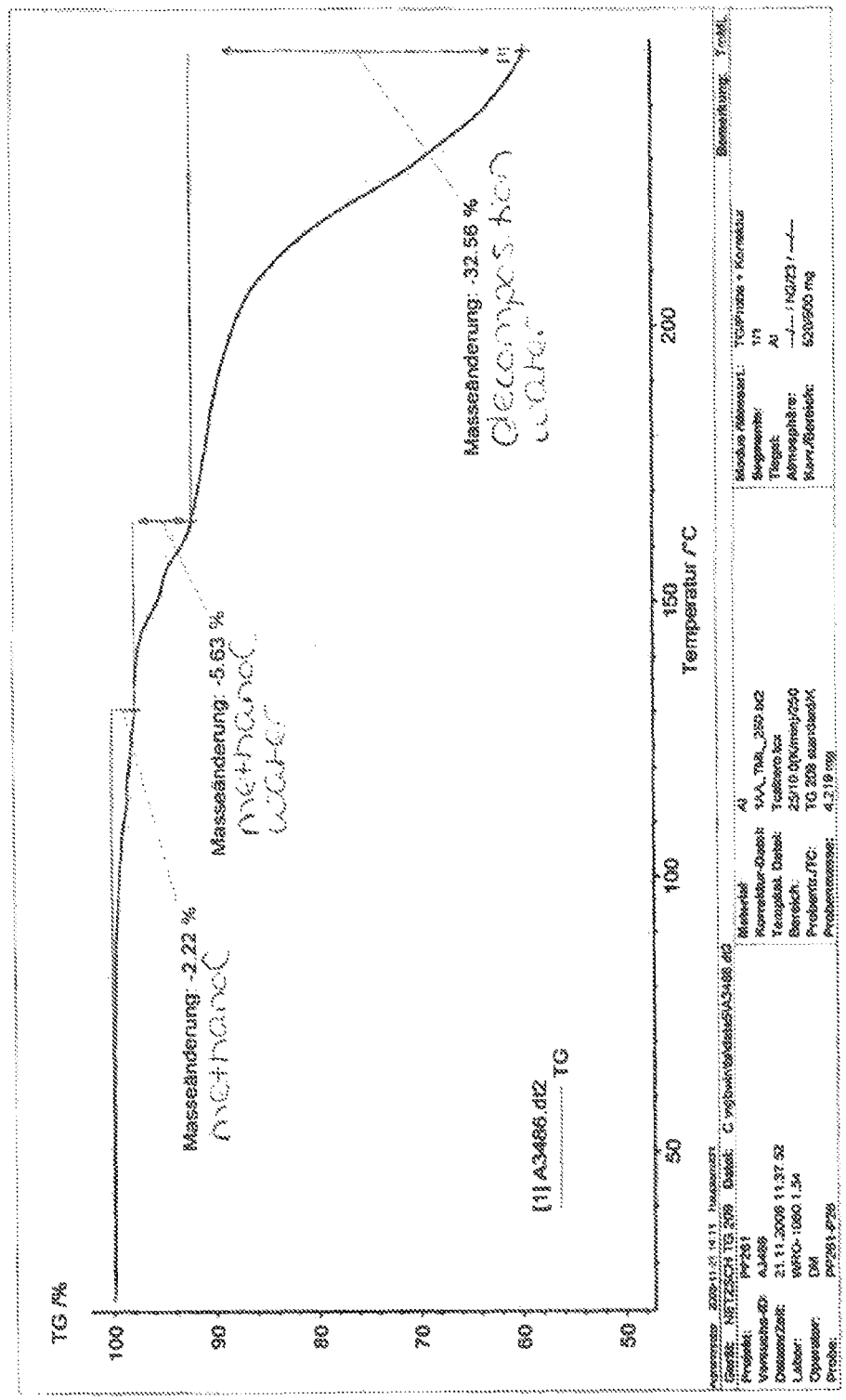
FIG. 15 shows a TG-FTIR spectrum of an amorphous sample of (−)-(2R,3S)-2-Amino-3-hydroxy-3-pyridin-4-yl-1-pyrrolidin-1-yl-propan-1-one-L-(+) tartrate. The sample contains approximately 8% MeOH and traces of water. Degradation was observed above 160° C.
Figure 16:
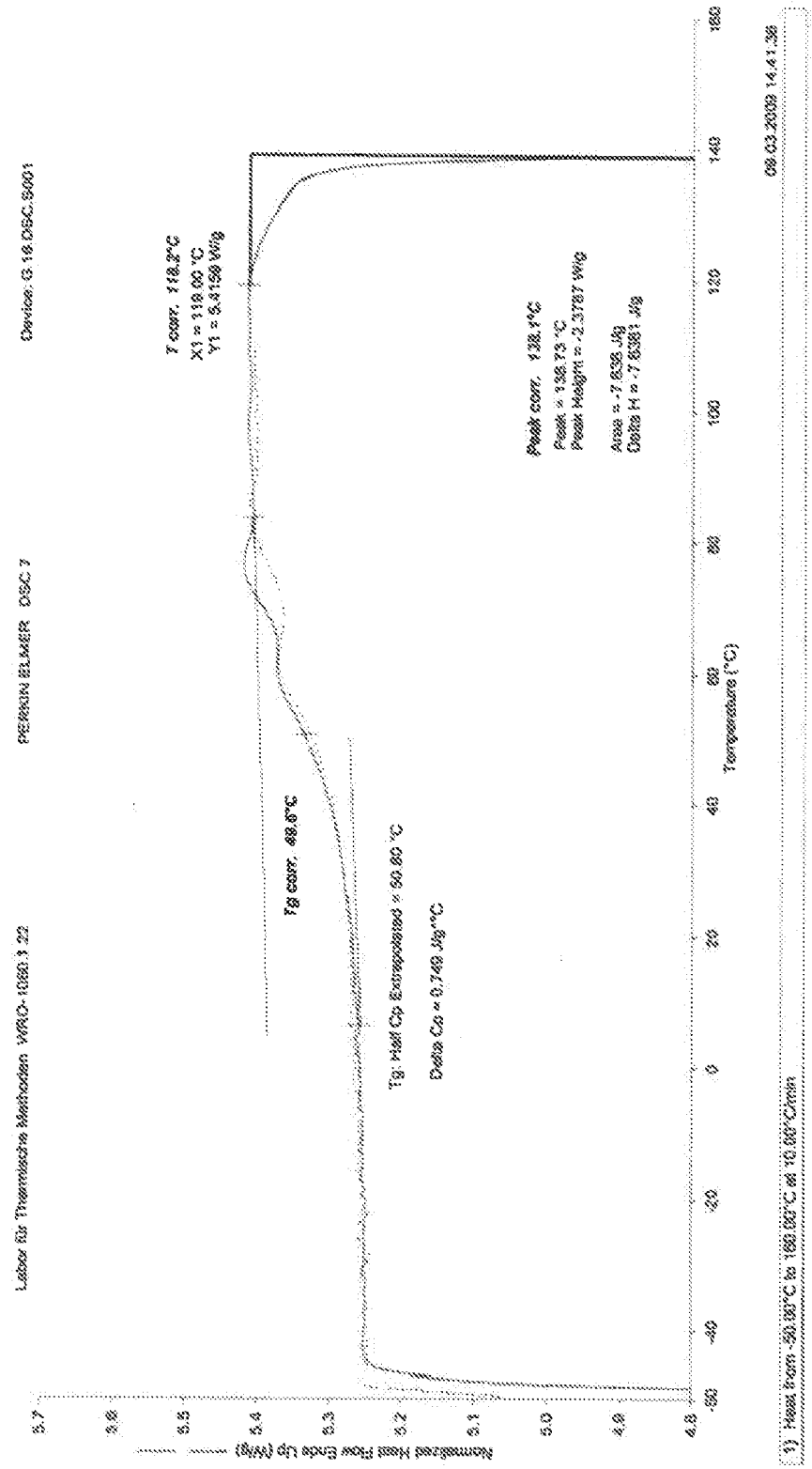
FIG. 16 shows a DSC scan of an amorphous sample of (−)-(2R,3S)-2-Amino-3-hydroxy-3-pyridin-4-yl-1-pyrrolidin-1-yl-propan-1-one-L-(+) tartrate. A glass transition was observed at 49.6° C. and degradation above 118° C.
Figure 17:
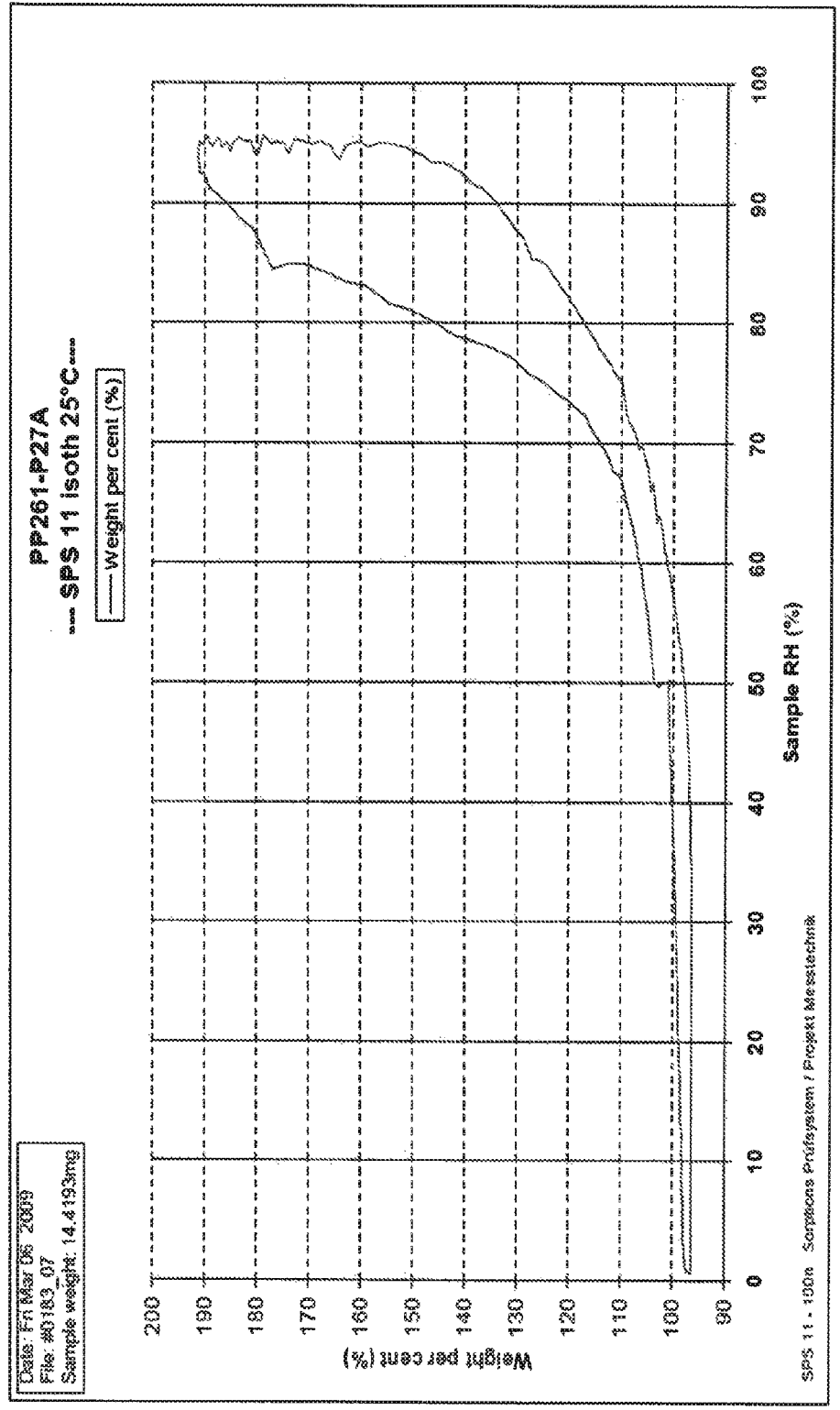
FIG. 17 shows a DVS spectrum of an amorphous sample of (−)-(2R,3S)-2-Amino-3-hydroxy-3-pyridin-4-yl-1-pyrrolidin-1-yl-propan-1-one-L-(+) tartrate. The sample is very hygroscopic and deliquescent. The deliquescence was visually confirmed. Additionally, the weight continued to increase even after r.h. had already started to decrease.

The salt of choice, (−)-(2R,3S)-2-amino-3-hydroxy-3-pyridin-4-yl-1-pyrrolidin-1-yl-propan-1-one (L)-(+) tartrate was subjected to polymorphism studies. Besides an amorphous form, two crystalline forms were obtained. Upon evaluation, it was determined that one of the crystalline forms was probably a mixture of the monotartrate with a degradation product. The most stable crystalline form was a single solvent-free crystalline form (form A) which was isolated, characterized and scaled up. Milling with a ball mill converts the crystalline form A into the amorphous form. The amorphous form was prepared by lyophilization from MeOH/$H_2O$ and characterized by FT Raman (FIG. 12), PXRD (Powder X-Ray Diffraction; FIG. 13), $^1$H-NMR (FIG. 14), TG-FTIR (Thermogravimetric analysis-Fourier-Transform-Infrared spectroscopy; FIG. 15), DSC (FIG. 16), and DVS (FIG. 17)

TABLE 1

Figure 6:
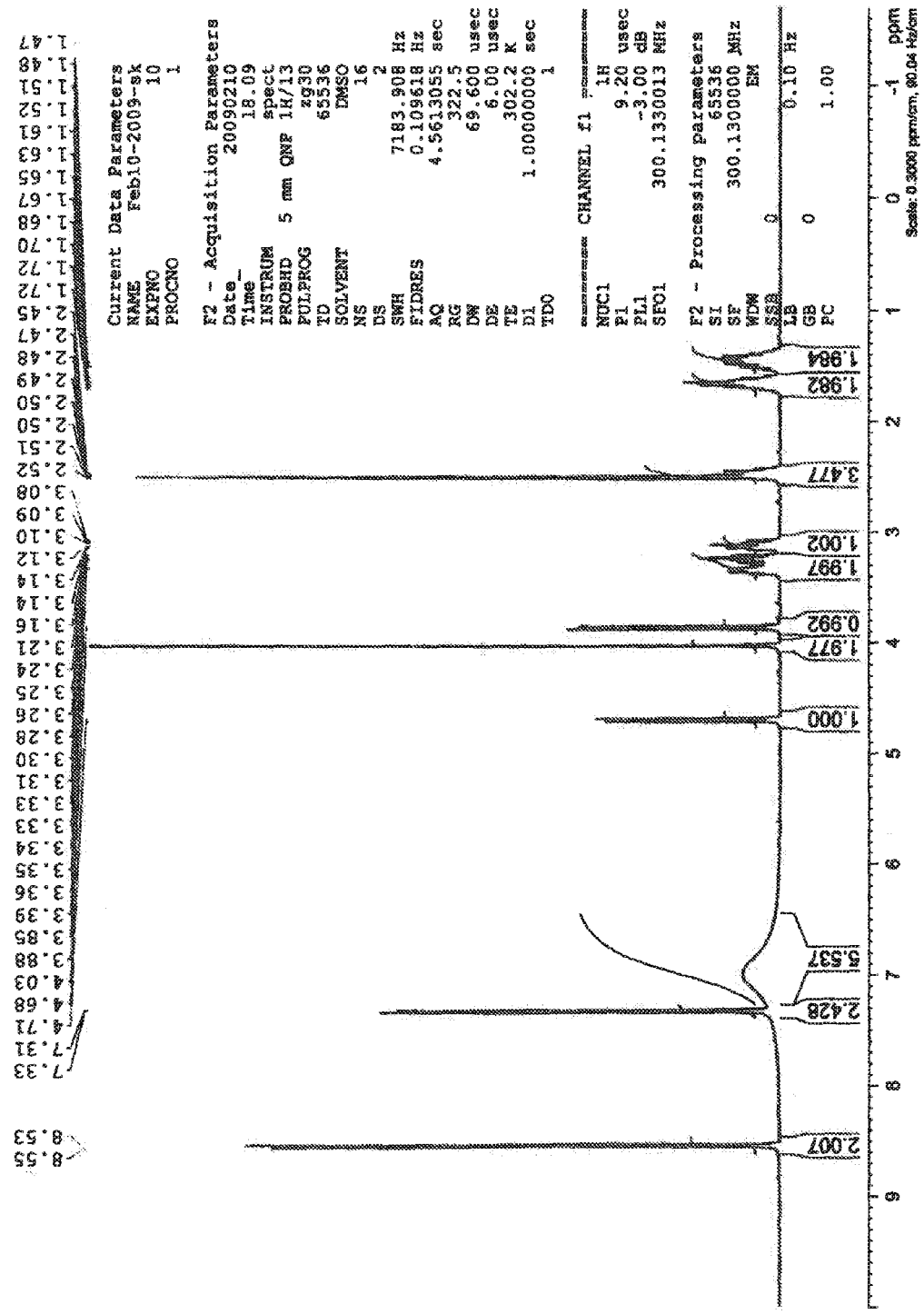
FIG. 6 shows a $^1$H-NMR (dmso-d6) spectrum of a purified crystalline sample (form A) of (−)-(2R,3S)-2-Amino-3-hydroxy-3-pyridin-4-yl-1-pyrrolidin-1-yl-propan-1-one L-tartrate. The chemical shifts, multiplicity integration and the chemical groups they represent are listed in Table 1.
Figure 7:
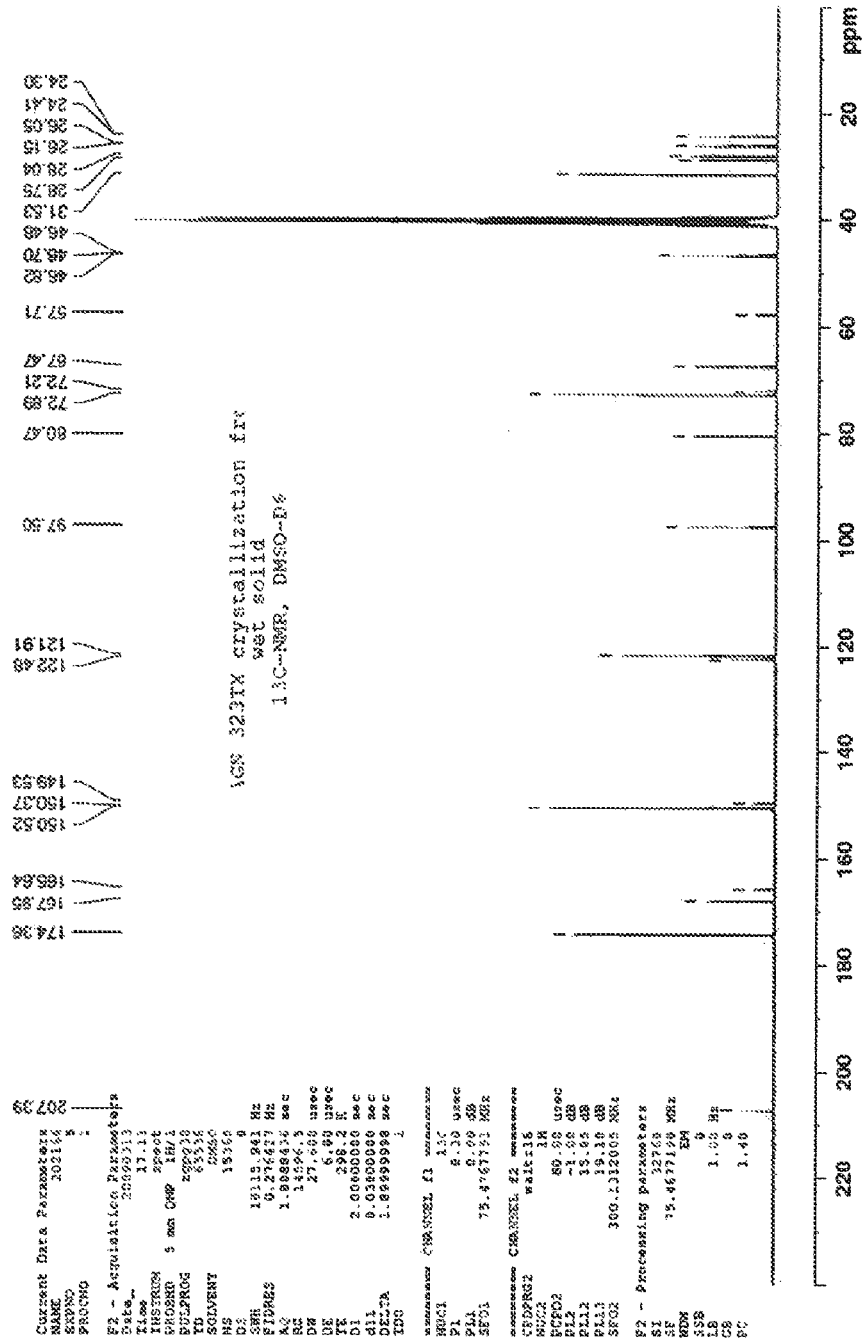
FIG. 7 shows a $^{13}$C NMR spectrum (dmso-d6) of a recrystallized sample of (−)-(2R,3S)-2-Amino-3-hydroxy-3-pyridin-4-yl-1-pyrrolidin-1-yl-propan-1-one L-(+)tartrate.

Peak details for the $^1$H-NMR specrum of FIG. 6

| chemical shift | multiplicity | integral | correlation |
|---|---|---|---|
| 8.55-8.53 | AA'XX' | 2 | pyridine |
| 7.33-7.31 | AA'XX' | 2 | pyridine |
| 7.5-6.5 | s (broad) | 5-6 | NH/OH |
| 4.70 | d | 1 | CHOH |
| 4.02 | s | 2 | CHOH (tartrate) |
| 3.86 | d | 1 | $CHNH_2$ |
| 3.4-3.2 | m | 2 | pyrrolidine |
| 3.2-3.1 | m | 1 | pyrrolidine |
| 2.5-2.4 | m | 5.7 | pyrrolidine + DMSO |
| 1.7-1.6 | m | 2 | pyrrolidine |
| 1.5-1.3 | m | 2 | pyrrolidine |

The ratio of the CHOH peaks of both compounds is 1:1. This confirms the salt stoichiometry of 1:1. s = singlet, d = doublet, m = multiplet

TABLE 2

Figure 8:
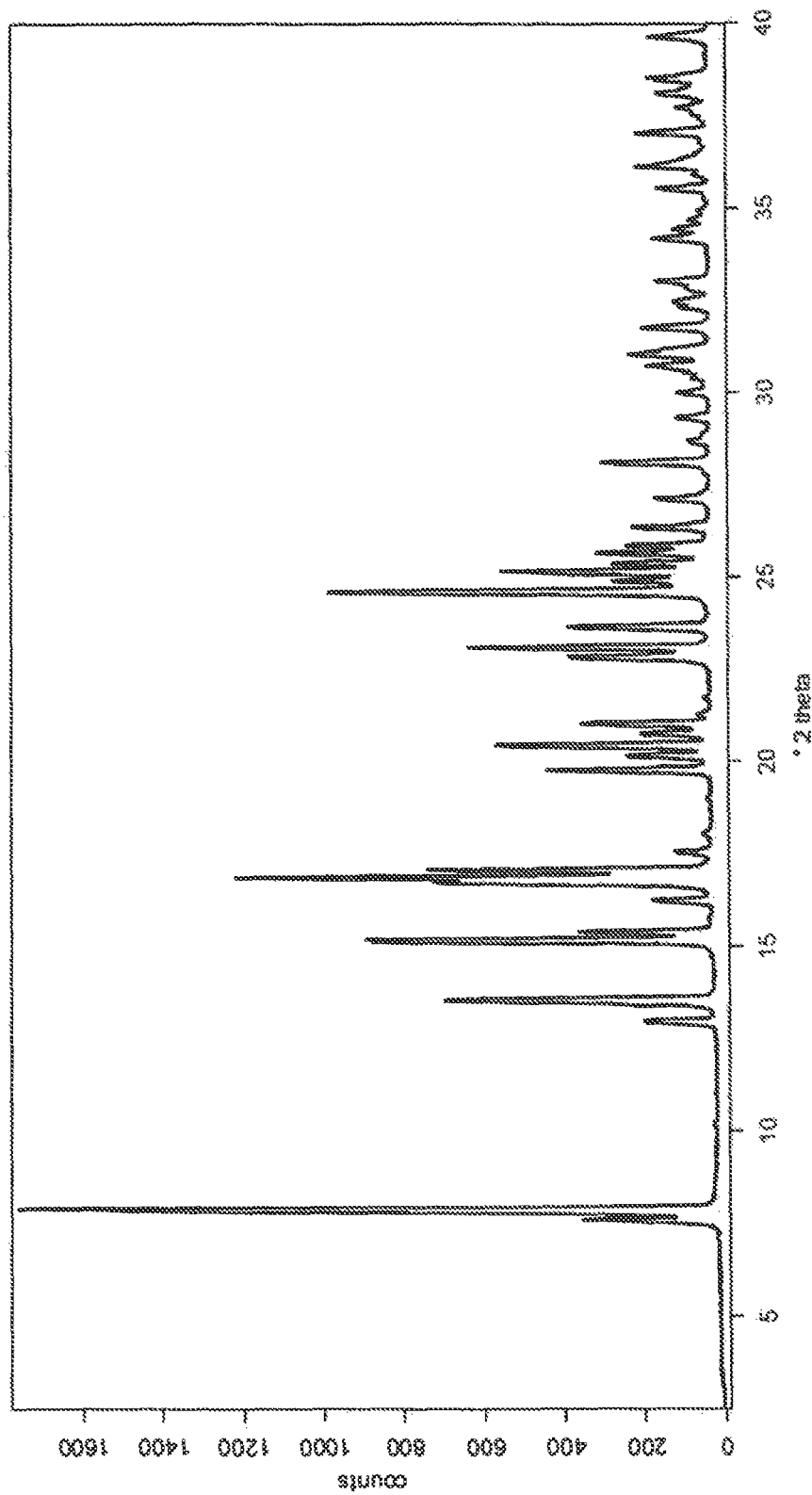
FIG. 8 shows the PXRD pattern of a purified sample of (−)-(2R,3S)-2-Amino-3-hydroxy-3-pyridin-4-yl-1-pyrrolidin-1-yl-propan-1-one L-(+)tartrate. The sample is crystalline and corresponds to form A. The peak details are provided in Table 2.
Figure 9:
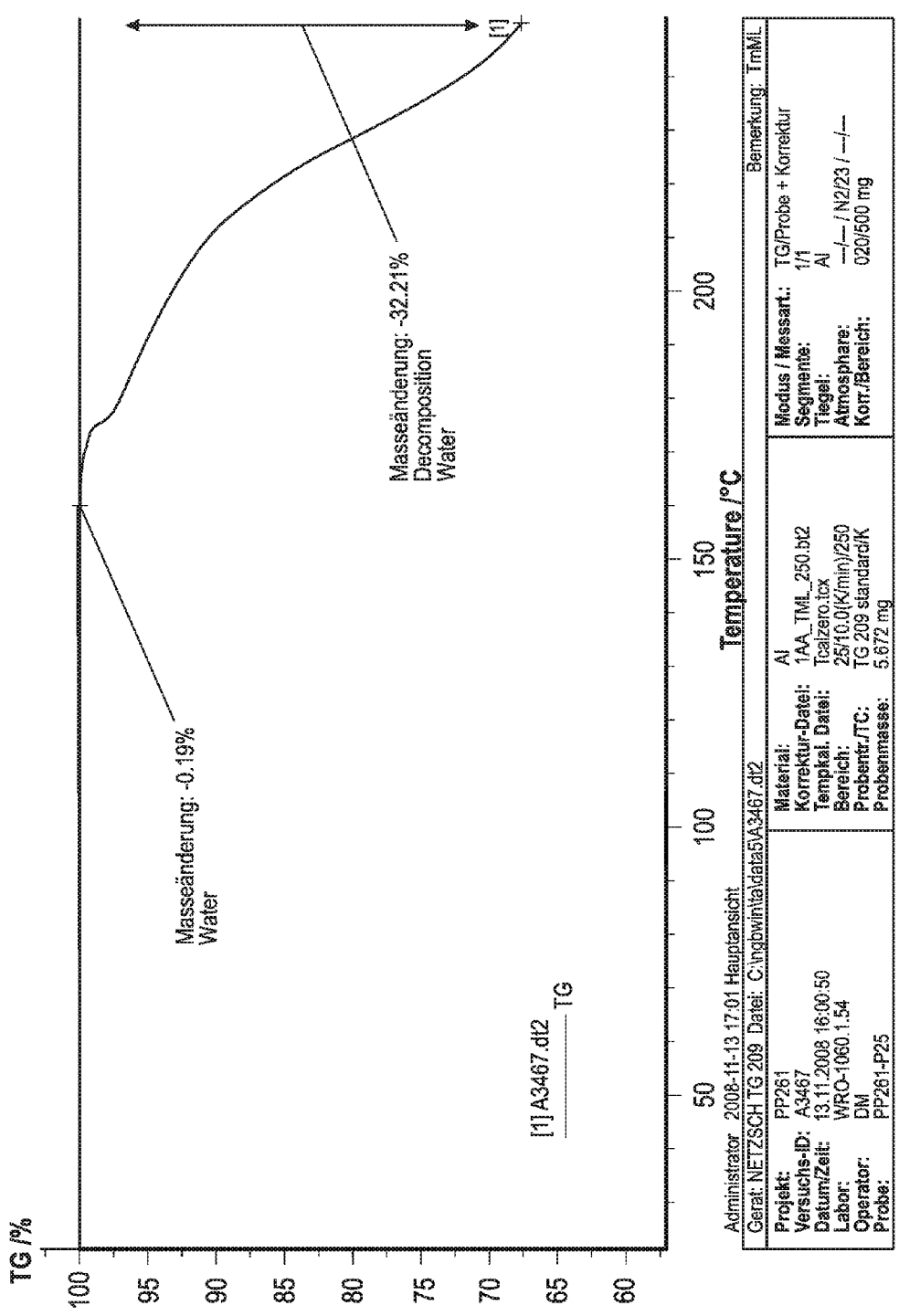
FIG. 9 shows a TG-FTIR spectrum of a sample of (−)-(2R,3S)-2-Amino-3-hydroxy-3-pyridin-4-yl-1-pyrrolidin-1-yl-propan-1-one L-(+)tartrate. The sample decomposed above 160° C. The released water vapor and possible gaseous degradation products were identified by FTIR spectroscopy.
Figure 10:
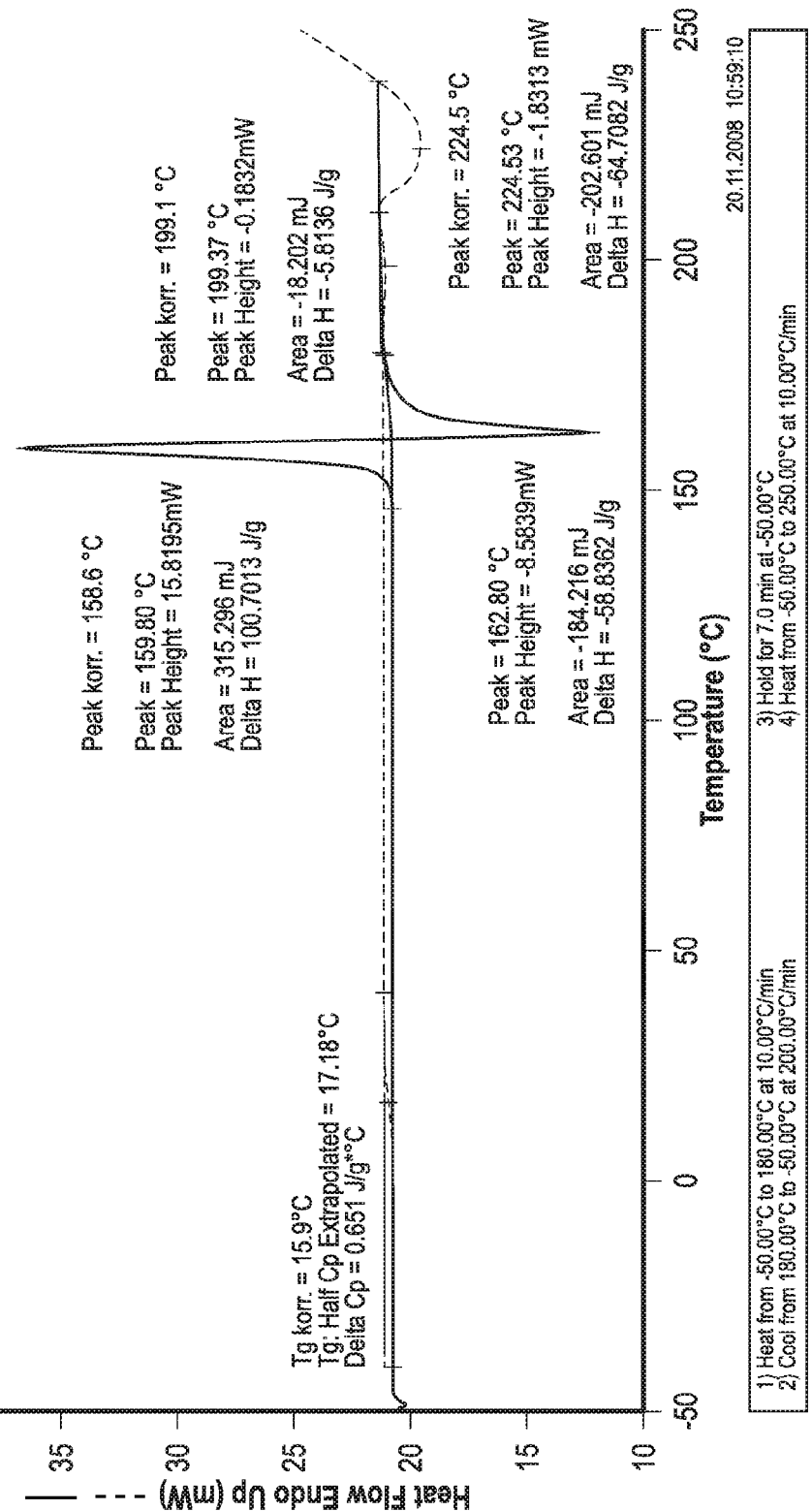
FIG. 10 shows a Differential Scanning calorimetry (DSC) of a sample of (−)-(2R,3S)-2-Amino-3-hydroxy-3-pyridin-4-yl-1-pyrrolidin-1-yl-propan-1-one-L-(+) tartrate. The first scan (solid line) shows overlapping melting and degradation at ~160° C., which agrees with the TG-FTIR results. The second scan (dotted line) shows only a glass transition ($T_g$) at 160° C. No crystallization was observed. The exothermic event at 225° C. observed in the second scan can be attributed to further degradation.
Figure 11:
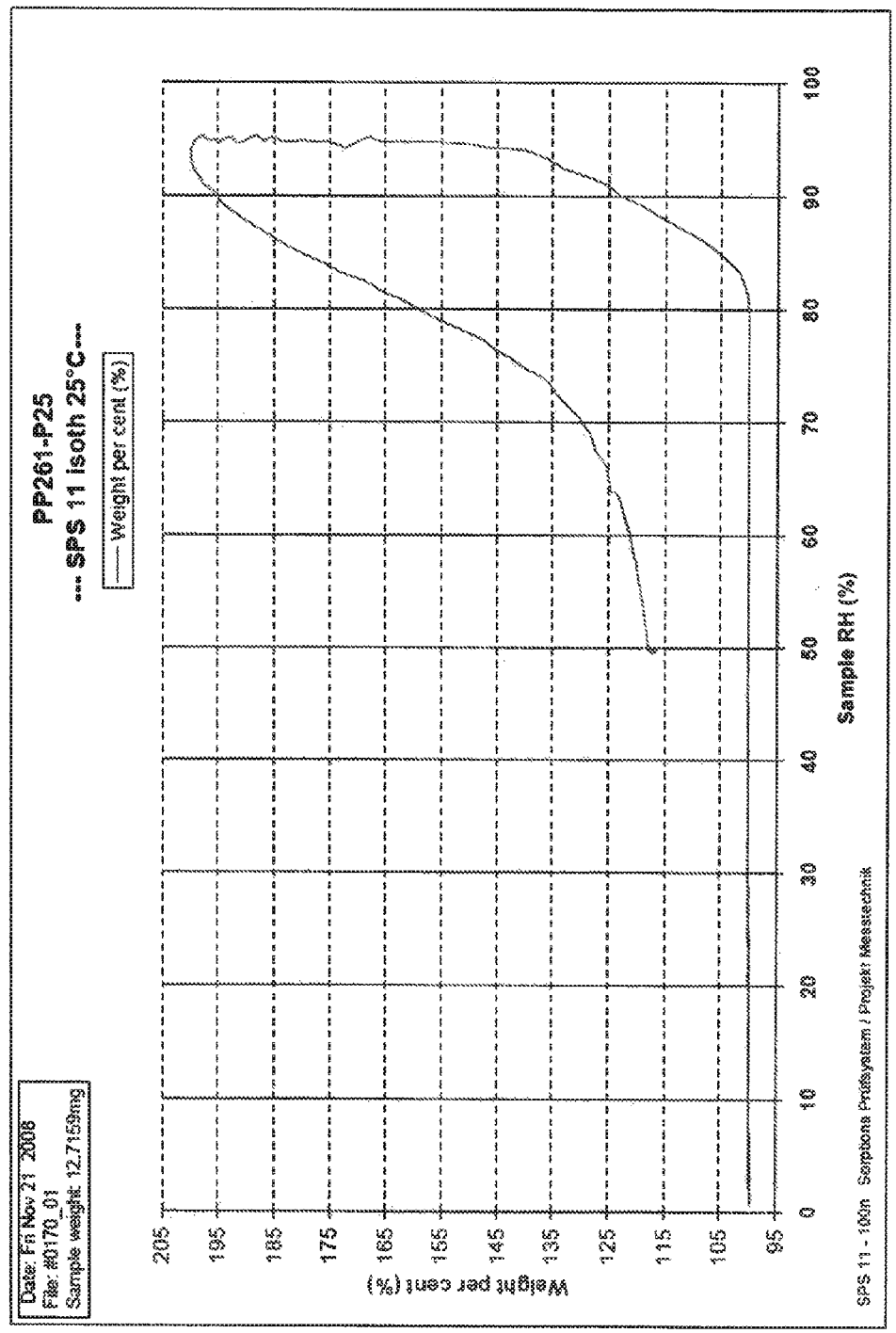
FIG. 11 shows a Dynamic Vapor Sorption (DVS) spectrum of a sample of (−)-(2R,3S)-2-Amino-3-hydroxy-3-pyridin-4-yl-1-pyrrolidin-1-yl-propan-1-one-L-(+) tartrate. The sample is very hygroscopic (water uptake above 80% r.h.) and deliquescent. The deliquescence was visually confirmed. Additionally, the weight continued to increase even after the relative humidity (RH) had already started to decrease.

Peak details for the PXRD pattern of FIG. 8

| angle °2 theta | d value Angstrom | intensity Cps | % |
|---|---|---|---|
| 7.61 | 11.6 | m | 21 |
| 7.89 | 11.2 | vs | 100 |
| 12.97 | 6.8 | w | 11 |
| 13.50 | 6.6 | s | 40 |
| 15.13 | 5.85 | s | 56 |
| 15.19 | 5.83 | s | 52 |
| 15.38 | 5.76 | m | 21 |
| 16.23 | 5.46 | w | 10 |
| 16.71 | 5.30 | s | 42 |
| 16.83 | 5.26 | vs | 72 |
| 17.05 | 5.20 | s | 44 |
| 17.56 | 5.05 | w | 7 |
| 18.05 | 4.91 | vw | 3 |
| 19.76 | 4.49 | m | 27 |
| 20.14 | 4.41 | w | 15 |
| 20.43 | 4.34 | s | 33 |
| 20.76 | 4.28 | w | 12 |
| 21.00 | 4.23 | m | 20 |
| 21.29 | 4.17 | vw | 4 |
| 21.70 | 4.09 | vw | 3 |
| 22.77 | 3.90 | m | 27 |
| 22.86 | 3.89 | m | 19 |
| 23.07 | 3.85 | s | 41 |
| 23.66 | 3.76 | m | 23 |
| 24.58 | 3.62 | s | 64 |
| 24.90 | 3.57 | m | 17 |
| 25.11 | 3.54 | s | 32 |
| 25.35 | 3.51 | m | 18 |
| 25.63 | 3.47 | m | 20 |
| 25.83 | 3.45 | m | 16 |
| 26.33 | 3.38 | w | 14 |
| 27.09 | 3.29 | w | 10 |
| 28.08 | 3.18 | m | 20 |
| 28.64 | 3.11 | w | 5 |
| 28.85 | 3.09 | vw | 3 |
| 29.31 | 3.04 | w | 8 |
| 29.99 | 2.98 | w | 7 |
| 30.39 | 2.94 | w | 5 |
| 30.53 | 2.93 | w | 7 |
| 30.71 | 2.91 | w | 12 |
| 31.02 | 2.88 | w | 14 |
| 31.17 | 2.87 | w | 8 |
| 31.72 | 2.82 | w | 13 |
| 32.30 | 2.77 | w | 7 |
| 32.45 | 2.75 | w | 8 |
| 32.78 | 2.73 | w | 6 |
| 33.00 | 2.71 | w | 11 |
| 34.15 | 2.62 | w | 12 |
| 34.41 | 2.60 | w | 8 |
| 34.68 | 2.59 | w | 6 |
| 34.92 | 2.57 | vw | 4 | vs = very strong; s = strong; m = medium; w = weak; vw = very weak

The monotartrate salt of the invention has analgesic and/or immunostimulant activity in mammals.

An art-accepted model or assay for measuring an analgesic effect of a compound in chronic pain (in particular peripheral neuropathy) is the model known as *Kim and Chung* 1992, Pain 150, pp 355-363 (Chung model). This model involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hind paw is moderately everted and the toes are held together. More importantly, the hind paw on the side affected by the surgery appears to become sensitive to low-threshold mechanical stimuli and will perceive pain instead of the faint sensation of touch. This sensitivity to normally non-painful touch, called "tactile allodynia", develops within the first week after surgery and lasts for at least two months. The allodynia response includes lifting the affected hind paw to escape from the stimulus, licking the paw and holding it in the air for many seconds. None of these responses is normally seen in the control group.

To produce the tactile allodynia, rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

After a complete hemostasis is confirmed, the wounds are sutured. A small amount of antibiotic ointment is applied to the incised area, and the rat is transferred to the recovery plastic cage under a regulated heat-temperature lamp.

On the day of the experiment, at least seven days after the surgery, typically six rats per test group are administered the test drugs by intraperitoneal (i.p.) injection or oral gavage (p.o.). For i.p. administration, the compounds are formulated in $H_2O$ and given in a volume of 1 ml/kg body weight by injecting into the intraperitoneal cavity. For p.o. administration, the compounds are formulated in $H_2O$ and given in a volume of 1 ml/kg body weight using an 18-gauge, 3 inch gavage needle that is slowly inserted through the esophagus into the stomach.

Tactile allodynia is assessed via von Frey hairs, which are a series of fine hairs with incremental differences in stiffness. Rats are placed in a plastic cage with a wire mesh bottom and allowed to acclimate for approximately 30 minutes. To establish the pre-drug baseline, the von Frey hairs are applied perpendicularly through the mesh to the mid-plantar region of the rats' hind paw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. Tactile allodynia is measured prior to and 15, 30, and 60 minutes after drug administration. The post-drug threshold is compared to the pre-drug threshold and the percent reversal of tactile sensitivity is calculated based on a normal threshold of 15.1 grams.

The monotartrate salt of the invention may be administered at pharmaceutically effective dosages. Such dosages are normally the minimum dose necessary to achieve the desired therapeutic effect; in the treatment of chronic pain, this amount would be roughly that necessary to reduce the discomfort caused by the pain to tolerable levels. For human adults such doses generally will be in the range 0.1-5000 mg/day; more preferably in the range 1 to 3000 mg/day, still more preferably in the range of 10 mg to 1000 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The salt of the present invention is useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, intraperitonial, parenteral, subcutaneous, intranasal, intrathecal, intramuscular, intravenous and intrarectal modes of delivery. Another aspect of the invention is drawn to therapeutic compositions comprising the novel compounds of the invention and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of the salt of the present invention to a mammal in need thereof. As indicated above, the compound will usually be formulated in a form consistent with the desired mode of delivery.

The salt of the present invention as an immunostimulant is administered subject to the same basic principles as compounds having analgesic activity, in doses which are best determined on a case-by-case and/or species-by-species and, in case of humans, at times on a patient-by-patient basis. Generally speaking the effective dose will be in the range of 10 µg/kg to 200 mg/kg.

The salt of the present invention may also be used to treat a cognitive disorder in a subject in need of such treatment. The dosage for such treatment for human adults such doses generally will be in the range 0.1-5000 mg/day; more preferably in the range 1 to 3000 mg/day, still more preferably in the range of 10 mg to 1000 mg/day. However, the actual amount of the compound to be administered in any given case will be determined by a physician taking into account the relevant circumstances, such as the severity of the cognitive disorder, the age and weight of the patient, the patient's general physical condition, the cause of the cognitive disorder, and the route of administration. Generally speaking the effective dose will be in the range of 10 µg/kg to 200 mg/kg.

The term "cognitive disorder," as used here, means any condition characterized by a deficit in mental activities associated with thinking, learning, or memory. Examples of such disorders include agnosias, amnesias, aphasias, apraxias, deliriums, dementias, and learning disorders.

In some cases, the cause of a cognitive disorder may be unknown or uncertain. In other cases, the cognitive disorder may be associated with (that is, be caused by or occur in the presence of) other conditions characterized by damage to or loss of neurons or other structures involved in the transmission of signals between neurons.

Hence, cognitive disorders may be associated with neurodegenerative diseases such as Alzheimer's disease, corticobasal degeneration, Creutzfeldt-Jacob disease, frontotemporal lobar degeneration, Huntington disease, multiple sclerosis, normal pressure hydrocephalus, organic chronic brain syndrome, Parkinson's disease, Pick disease, progressive supranuclear palsy, or senile dementia (Alzheimer type); it may be associated with trauma to the brain, such as that caused by chronic subdural hematoma, concussion, intracerebral hemorrhage, or with other injury to the brain, such as that cause by infection (e.g., encephalitis, meningitis, septicemia) or drug intoxication or abuse.

Cognitive disorders may also be associated with other conditions which impair normal functioning of the central nervous system, including psychiatric disorders such as anxiety disorders, dissociative disorders, mood disorders, schizophrenia, and somatoform and factitious disorders; it may also be associated with conditions of the peripheral nervous system, such as chronic pain.

The salt of this invention may be used to treat agnosias, amnesias, aphasias, apraxias, deliriums, dementias, learning disorders and other cognitive disorders regardless of whether their cause is known or not. Examples of dementias which may be treated with the salt of the present invention include AIDS dementia complex, Binswanger's disease, dementia with Lewy Bodies, frontotemporal dementia, multi-infarct dementia, Pick's disease, semantic dementia, senile dementia, and vascular dementia.

Examples of learning disorders which may be treated with the salt of the present invention include Asperger's syndrome, attention deficit disorder, attention deficit hyperactivity disorder, autism, childhood disintegrative disorder, and Rett syndrome.

Examples of aphasia which may be treated with the salt of the present invention include progressive non-fluent aphasia.

The salt of the present invention also be used to treat patient having deficits in mental activities that are mild or that otherwise do not significantly interfere with daily life. Mild cognitive impairment is an example of such a condition: a patient with mild cognitive impairment displays symptoms of dementia (e.g., difficulties with language or memory) but the severity of these symptoms is such that a diagnosis of dementia may not be appropriate. The salt may be used to treat mild cognitive impairment and other, similarly less severe forms of cognitive disorders.

Each and every reference disclosed herein is incorporated by reference herein for all purposes.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

What is claimed is:

1. A salt that is (−)-(2R,3S)-2-amino-3-hydroxy-3-pyridin-4-yl-1-pyrrolidin-1-yl-propan-1-one (L)-(+) tartrate salt in crystalline form and having an X-ray powder diffraction spectrum with peaks expressed in degrees (2θ) at approximately 7.61, 7.89, 12.97, 13.50, 15.13, 15.19, 15.38, 16.23, 16.71, 16.83, 17.05, 19.76, 20.14, 20.43, 20.76, 21.00, 22.77, 22.86, 23.07, 23.66, 24.58, 24.90, 25.11, 25.35, 25.63, 25.83, 26.33, 27.09, 28.08, 30.71, 31.02, 31.72, 33.00 and 34.15.

2. A pharmaceutical composition comprising the tartrate salt of claim 1, and at least one pharmaceutically acceptable carrier.

3. A method of treating pain in a mammal, said method comprising administering to said mammal in need thereof, a therapeutically effective amount of the salt of claim 1.

4. The method of claim 3, wherein said pain is chronic pain.

5. A method of treating a cognitive disorder in a mammal, said method comprising administering to said mammal in need thereof, a therapeutically effective amount of the salt of claim 1, and wherein the cognitive disorder is selected from the group consisting of an agnosia, an amnesia, an aphasia, an apraxia, a delirium, a dementia, a learning disorder, AIDS dementia complex, Binswanger's disease, dementia with Lewy Bodies, frontotemporal dementia, mild cognitive impairment, multi-infarct dementia, Pick's disease, semantic dementia, senile dementia, vascular dementia, a cognitive disorder associated with neurodegenerative disease, a cognitive disorder associated with injury to the brain, a cognitive disorder associated with psychiatric disorders, and a cognitive disorder associated with chronic pain.

6. The method of claim 5, wherein the learning disorder is selected from the group consisting of Asperger's syndrome, attention deficit disorder, attention deficit hyperactivity disorder, autism, childhood disintegrative disorder, and Rett syndrome.

7. The method of claim 5, wherein the aphasia is progressive non-fluent aphasia.

8. The method of claim 5, wherein the neurodegenerative disease is selected from the group consisting of Alzheimer's disease, corticobasal degeneration, Creutzfeldt-Jacob disease, frontotemporal lobar degeneration, Huntington disease, multiple sclerosis, normal pressure hydrocephalus, organic chronic brain syndrome, Parkinson's disease, Pick disease, progressive supranuclear palsy, and senile dementia.

9. The method of claim 8, wherein the senile dementia is Alzheimer type.

10. The method of claim 5, wherein the injury to the brain is selected from the group consisting of chronic subdural hematoma, concussion, intracerebral hemorrhage, encephalitis, meningitis, septicemia, drug intoxication, and drug abuse.

11. The method of claim 5, wherein the psychiatric disorders are selected from the group consisting of anxiety disorders, dissociative disorders, mood disorders, schizophrenia, and somatoform and factitious disorders.

* * * * *